United States Patent [19]

Sopori et al.

[11] Patent Number: 5,757,474
[45] Date of Patent: May 26, 1998

[54] SYSTEM FOR CHARACTERIZING SEMICONDUCTOR MATERIALS AND PHOTOVOLTAIC DEVICES THROUGH CALIBRATION

[75] Inventors: Bhushan L. Sopori, Denver; Larry C. Allen, Arvada; Craig Marshall, Littleton; Robert C. Murphy, Golden; Todd Marshall, Littleton, all of Colo.

[73] Assignee: Midwest Research Institute, Kansas City, Mo.

[21] Appl. No.: 496,061

[22] Filed: Jun. 28, 1995

Related U.S. Application Data

[63] Continuation-in-part of Ser. No. 314,201, Sep. 28, 1994, Pat. No. 5,581,346, which is a continuation-in-part of Ser. No. 60,301, May 10, 1993, Pat. No. 5,406,367.

[51] Int. Cl.⁶ ................................................. G01N 21/88
[52] U.S. Cl. .......................... 356/72; 356/30; 356/237; 356/446
[58] Field of Search .................. 356/30, 31, 237, 356/445, 446, 243, 448, 72, 73; 250/214 SG

[56] References Cited

U.S. PATENT DOCUMENTS

| | | | |
|---|---|---|---|
| 4,175,981 | 11/1979 | Loutfy et al. | 250/214 SG |
| 4,243,473 | 1/1981 | Yamaguchi et al. | 156/626 |
| 4,259,020 | 3/1981 | Babb | 356/243 |
| 4,329,052 | 5/1982 | Colombo et al. | 356/335 |
| 4,482,245 | 11/1984 | Makabe et al. | 356/30 |
| 4,626,101 | 12/1986 | Ogawa et al. | 356/237 |
| 4,677,298 | 6/1987 | Zelmanovic et al. | 356/446 |
| 4,794,265 | 12/1988 | Quackenbos et al. | 250/572 |
| 4,840,487 | 6/1989 | Noguchi et al. | 356/355 |
| 4,925,298 | 5/1990 | Dobrilla | 356/30 |
| 5,008,542 | 4/1991 | Look et al. | 250/341 |

FOREIGN PATENT DOCUMENTS

| | | | |
|---|---|---|---|
| 3-214043 | 9/1991 | Japan | 356/448 |

OTHER PUBLICATIONS

B.L. Sopori, Use of Optical Scattering to Characterize Dislocations in Semiconductors, 22 Appl. Optics 4676 (1988).

B.L. Sopori, "A New Etch for Polycrystalline Silicon," J.Electrochem. Soc.: Solid–State Science and Technology, vol. 131, No. 3, p. 667 (1984).

*Primary Examiner*—F. L. Evans
*Attorney, Agent, or Firm*—Edna M. O'Connor; Ken Richardson

[57] ABSTRACT

A method and apparatus for measuring characteristics of a piece of material, typically semiconductor materials including photovoltaic devices. The characteristics may include dislocation defect density, grain boundaries, reflectance, external LBIC, internal LBIC, and minority carrier diffusion length. The apparatus includes a light source, an integrating sphere, and a detector communicating with a computer. The measurement or calculation of the characteristics is calibrated to provide accurate, absolute values. The calibration is performed by substituting a standard sample for the piece of material, the sample having a known quantity of one or more of the relevant characteristics. The quantity measured by the system of the relevant characteristic is compared to the known quantity and a calibration constant is created thereby.

12 Claims, 36 Drawing Sheets

(13 of 36 Drawing(s) in Color)

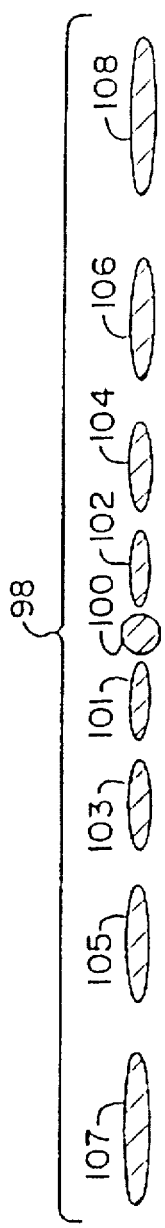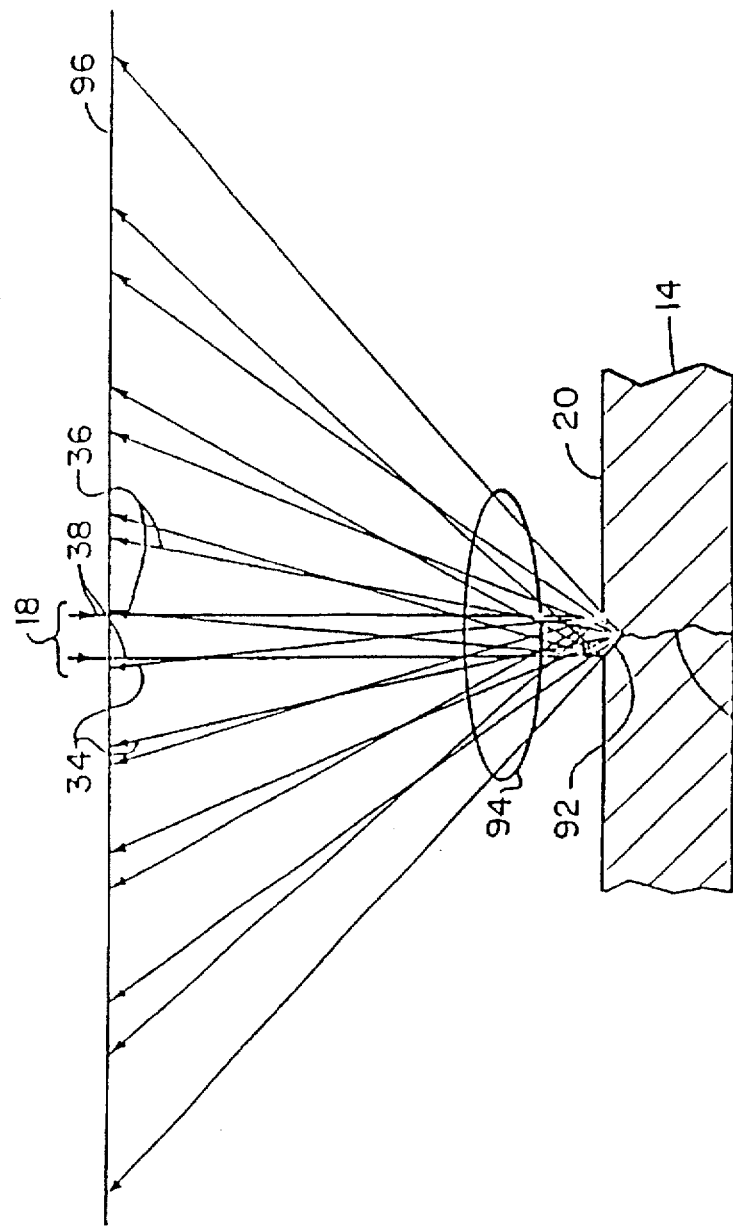

Specify the step size or distance between sample points

This is expressed in inches—for example: 0.005

Enter the step size  0.005
0.001 to 0.010

● Display step in Inches
○ Display step in Microns

Is the above step size correct?

Yes

Use default value of 0.005 inches

Select display color sequence

Select display color signal levels

Return to main menu

Figure 21

| Dis. density | Grain bndry. | LBIC | Spec. reflect. | Diff. reflect. |
|---|---|---|---|---|
| 140 | 120 | 3370 | 150 | 140 |
| 130 | 110 | 3360 | 148 | 130 |
| 120 | 100 | 3350 | 144 | 120 |
| 110 | 90 | 3340 | 142 | 110 |
| 100 | 80 | 3330 | 141 | 100 |
| 90 | 70 | 3320 | 140 | 90 |
| 80 | 60 | 3310 | 139 | 80 |
| 70 | 50 | 3300 | 138 | 70 |
| 60 | 40 | 3290 | 137 | 60 |
| 50 | 30 | 3280 | 136 | 50 |
| 40 | 20 | 3270 | 135 | 40 |
| 30 | 10 | 3260 | 134 | 30 |
| 20 | 5 | 3250 | 133 | 20 |
| 10 | 0 | 3240 | 132 | 10 |
| 0 | -50 | 3230 | 131 | 0 |
| -150 | -60 | 3220 | 130 | -150 |
| Save | Save | Save | Save | Save |

These buttons put the selection in the permanent file

Laser 1 pwr
800 Value saved
0 Value now
Recalibrate?

Laser 2 pwr
400 Value saved
0 Value now
Recalibrate?

Return to main menu

Print this

Figure 23

| Select from the options below | Select from the options below |
|---|---|
| Options<br>⦿ Laser 1, 630 nm<br>○ Laser 2, 905 nm | Options<br>⦿ Laser 1, 630 nm<br>○ Laser 2, 905 nm<br>○ Both lasers<br>○ Etch pit size correction |
| Laser 1 is the 630 nm red laser | Laser 1 is the 630 nm red laser |
| Continue with the scan | Continue with the scan |
| Return to main menu | Return to main menu |

Figure 24

SYSTEM FOR CHARACTERIZING SEMICONDUCTOR MATERIALS AND PHOTOVOLTAIC DEVICES THROUGH CALIBRATION

This application is a continuation-in-part of Ser. No. 08/314,201, filed on Sep. 28, 1994 (now issued as U.S. Pat. No. 5,581,346 on Dec. 3, 1996), entitled "System for Characterizing Semiconductor Materials and Photovoltaic Devices," which application is in turn a continuation-in-part of Ser. No. 08/060,301, filed on May 10, 1993 (now issued as U.S. Pat. No. 5,406,367 on Apr. 11, 1995), entitled "Improved Defect Mapping System."

CONTRACTUAL ORIGIN OF THE INVENTION

The United States Government has rights in this invention under Contract No. DE-AC36-83CH10093 between the U.S. Department of Energy and the National Renewable Energy Laboratory, a Division of Midwest Research Institute.

BACKGROUND OF THE INVENTION

1. Field of the Invention

This invention is related generally to improved techniques for mapping defects on semiconductor surfaces and characterizing photovoltaic devices and more particularly to an improved optical system that can more effectively distinguish dislocation pits from grain boundaries in mapping polycrystalline device surfaces and that can produce maps of the internal photoresponse of photovoltaic devices by using data from maps produced of the reflectance and external photoresponse of photovoltaic devices, the improvement relating primarily to compensation methods.

2. Description of the Prior Art

The quality and suitability of single crystalline and polycrystalline materials, such as silicon, gallium-arsenic, and others, for use as substrates for semiconductor applications are affected by defects, such as dislocations, in the crystalline structures. Generally, higher densities of dislocations are indicative of lower quality materials. Therefore, there is a need for systems to detect, measure, and map dislocation densities in single crystalline and polycrystalline materials for purposes of analysis and quality control.

There are a number of systems that have been developed to detect and map dislocation densities. The methods used most commonly in the industry currently utilize a surface cleaning or polish step followed by some variation of an etch, which reveals dislocations that intersect the surface of the material by forming a pit at each dislocation site. The pits can then be detected, counted, and mapped, and the density of the pits, i.e., number of pits per unit of surface area, can be determined. This etch pit density (EPD) is considered by persons skilled in this art to be a reliable indicator of the number and density of dislocations in the substrate, and the pits have patterns that reflect slip planes in the crystal lattice of the material.

The most commonly used method of detecting and counting pits to determine EPD is visual observation through a microscope and counting. This process is obviously labor intensive, time consuming, and tedious work. Some alternative systems based on optical technologies to detect and map EPDs have been developed that apparently work on monocrystalline substrates, but none that work reliably for polycrystalline substrates. For example, the U.S. Pat. No. 4,925,298, issued to P. Dobrilla, compares specularly reflected light from an etched sample surface to light reflected from a reference surface to determine EPD. U.S. Pat. No. 5,008,542, issued to D. Look et al. is similar, except it detects light transmitted through the substrate rather than reflected light. In both of those techniques, the specular light is detected, so increase of dislocation density results in increase of scattered light, thus decrease in detection signal. However, polycrystalline substrates present major problems for those systems, because grain boundaries cause substantial light scattering, thus affecting light detection signals and skewing EPD measurements.

It has also been shown and is now well-known in the industry that light scattering from a defect-etched surface can be used to determine surface dislocation numbers statistically. In fact, as reported in B. L. Sopori, "Use of Optical Scattering to Characterize Dislocations in Semiconductors," 22 APPL OPTICS 4676 (1988), it has been determined that the total integrated light scattered from an illuminated region of a defect-etched surface is proportional to the number of dislocation etch pits in that area, provided that the surface is etched for defect delineation. A light integrating sphere positioned on the surface of the material collects and integrates substantially all of the scattered light, and a photodetector mounted in the integrating sphere measures the integrated light intensity, thus the extent of EPD in an illuminated area on the surface. Again, however, while that large beam statistical EPD detection and mapping technique works well for many applications involving single crystalline materials, it does not work well with polycrystalline structures. Grain boundaries in polycrystalline materials are "grooved" in the defect etching process required for defect delineation, so scattering of light by the grain boundaries can cause a larger amplitude integrated light in the integrating sphere, thus an erroneous EPD signal.

Finally, at the present time there is no method known to provide maps of reflectance, external photoresponse, internal photoresponse, and other parameters relating to polycrystalline cells, such as efficiency of conversion, minority carrier diffusion length, and depth-dependent photoresponse. These maps can contribute valuable information on the effectiveness of the cell and also of the etching process. Importantly, for each of the above-mentioned measurements, maps, and calculations, most of the previous efforts have been directed toward relative rather than absolute values.

SUMMARY OF THE INVENTION

A general object of this invention, therefor, is to provide an improved defect mapping system for crystalline materials.

Another general object of this invention is to provide a defect mapping system that is useable and accurate on polycrystalline materials as well as single crystalline materials.

A more specific object of this invention is to provide an optical scattering defect mapping system wherein light scattered by etched dislocation pits can be discriminated from light scattered by grain boundaries.

Another specific object of this invention is to provide an improvement to large beam statistical EPD detection and mapping systems that can be used on both single crystalline and polycrystalline materials.

An even more specific object of this invention is to provide an improved large beam statistical EPD detection and mapping system that can be adjusted to detect and map either EPD or grain boundaries of a polycrystalline material.

Another specific object of this invention is to provide an EPD mapping system that corrects for variations in etch pit size in polycrystalline material from sample to sample.

Another specific object of the present invention is to provide a detection and mapping system with an increased ability to distinguish between EPD and grain boundaries of a polycrystalline material.

Still another specific object of this invention is to provide a method for producing maps of different parameters of polycrystalline materials and devices, such as reflectance and photoresponse maps.

Still another specific object of this invention is to provide a technique for producing defect maps, reflectance maps, and conversion efficiency maps in accurate, absolute values.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

To achieve the foregoing and other objects and in accordance with the purposes of the present invention, as embodied and broadly described therein, a defect mapping system includes a method for scattering light from the surface of a crystalline material that contains two types of defects, for example, dislocation defects and grain boundary defects, such that the first type of defect scatters light in a first pattern, and the second type of defect scatters light in a second pattern by using two different light beams. The light for detecting the first type of defect is provided by a relatively wide beam having a relatively long wavelength. The light for detecting the second type of defect is provided by a relatively narrow beam having a relatively short wavelength. The light of the first pattern is captured in a light integrating sphere for detection. The light of the second pattern is near specular and is passed through the light integrating sphere for separate detection. An accurate calculation of the magnitudes of the first defect and of the second defect is obtained by compensating for inaccuracies by substituting a standard sample for the crystalline material, the sample having a known magnitude of each of the first and second types of defect and using the ratio of the known magnitude of the defect to the indicated magnitude from the detected light as a compensation factor for the calculation of each of the first and second types of defect.

In addition, the present invention is directed to a method of and apparatus for measuring characteristics of a piece of material. The method includes exposing the piece of material to incoming light of a known level of power, determining the power level of the light reflected from the piece of material, calculating the amount of light absorbed by the piece of material based upon the power level of the light exposed and the power level of the light reflected, and compensating for inaccuracies in the known level of power and in the determination of the power level of the reflected light to achieve a compensated calculation of the amount of light absorbed.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The accompanying drawings, which are incorporated in and form a part of the specifications, illustrate the preferred embodiments of the present invention, and together with the descriptions serve to explain the principles of the invention.

In the Drawings:

FIG. 1 is a schematic diagram of the improved defect mapping system of the present invention;

FIG. 2 is an enlarged schematic illustration of the optical components of the system shown in FIG. 1;

FIG. 3a is a schematic representation of the scattered light rays from an illuminated crystalline material sample that has an etched surface to reveal and delineate defects, particularly dislocations, in the crystalline material;

FIG. 3b is a representation of a typical scattered light pattern from an illuminated crystalline sample that has been etched according to this invention;

FIG. 3c is an enlarged view of etch pits on the surface of a silicon sample, wherein the etch pits are substantially circular in shape;

FIG. 3d is a photograph of an actual light pattern that has been scattered by the surface of the silicon sample of FIG. 3c according to this invention;

FIG. 3e is an enlarged view of etch pits on the surface of a silicon sample, wherein the etch pits are substantially elliptical in shape;

FIG. 3f is a photograph of an actual light pattern that has been scattered by the surface of the silicon sample of FIG. 3e;

FIG. 3g is an enlarged view of etch pits on the surface of a silicon sample, wherein the etch pits are two different shapes (resembling ellipses);

FIG. 3h is a photograph of an actual light pattern that has been scattered by the surface of the silicon sample of FIG. 3g;

FIG. 4a is a schematic illustration of light rays scattered by a V-shaped etch grain boundary in a polycrystalline material;

Figure 2:
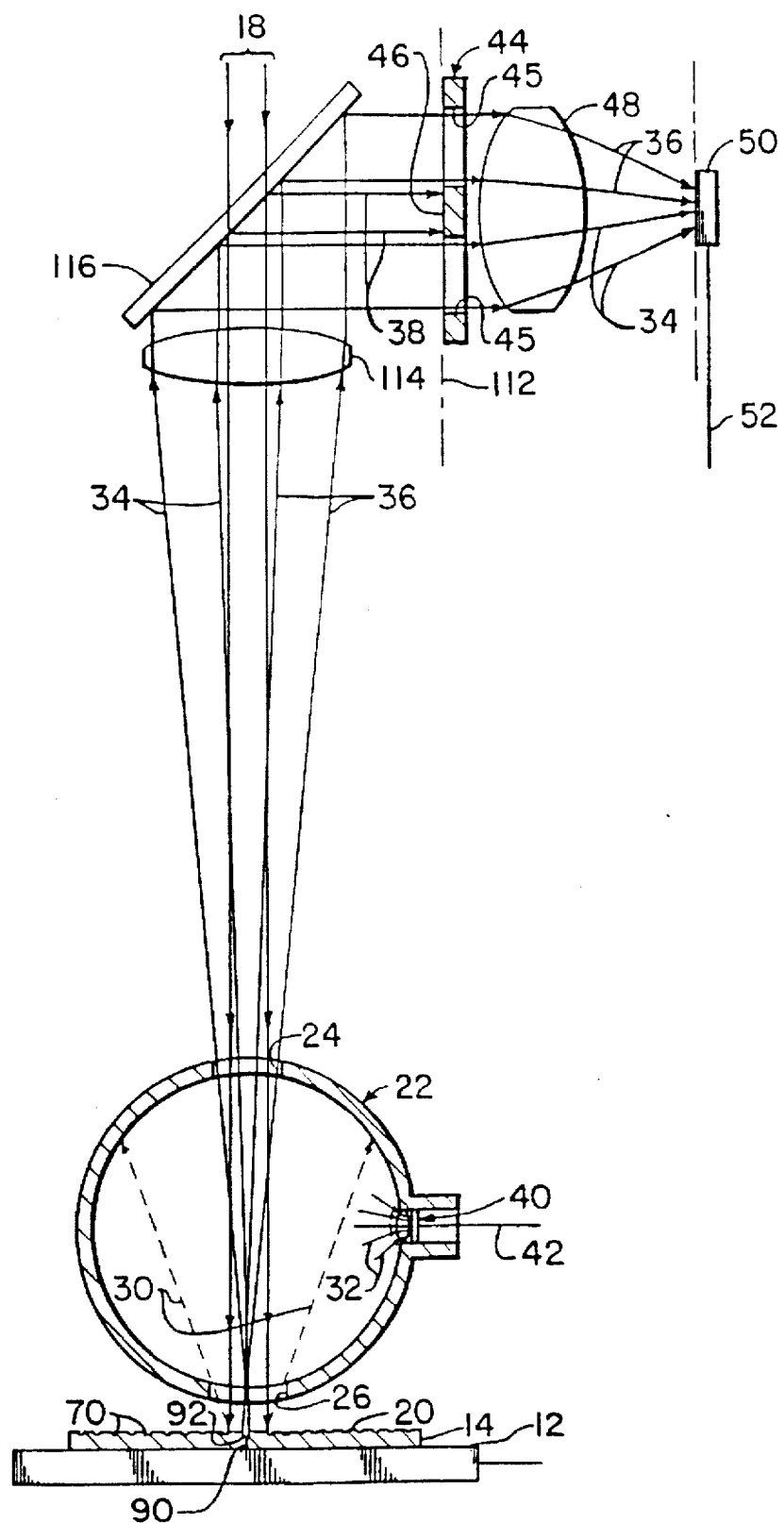
Figure 3B:
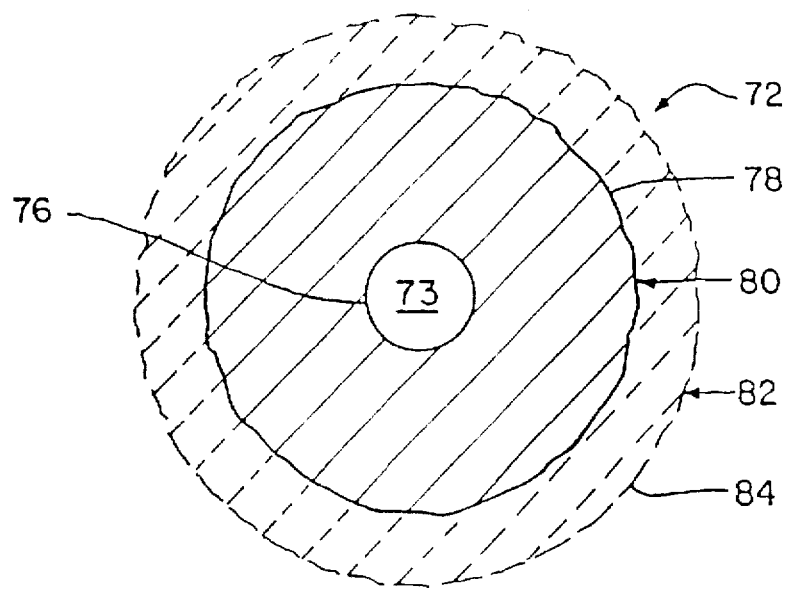
Figure 5:
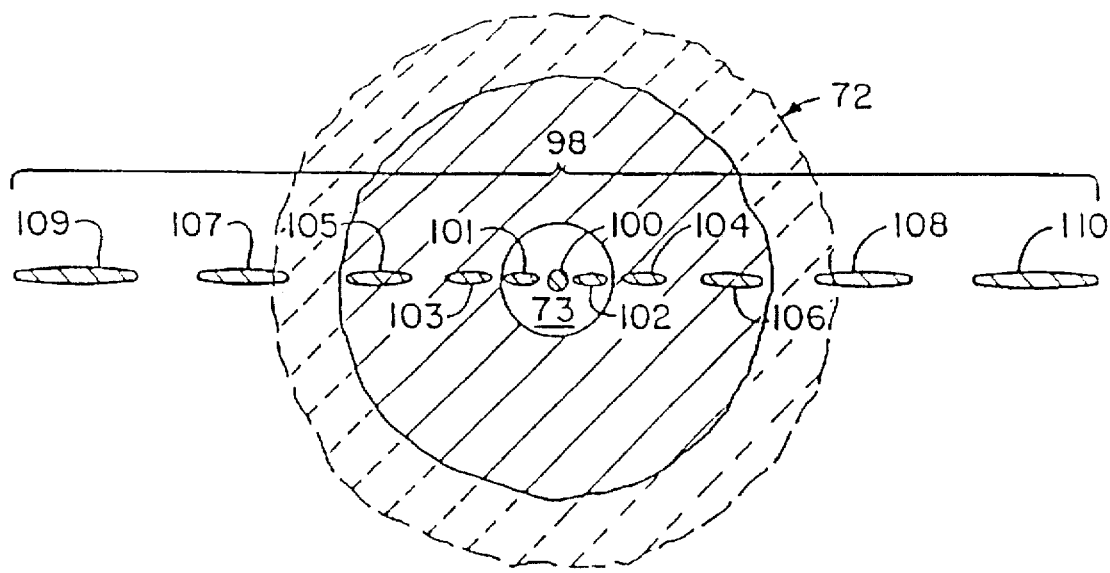
Figure 6:
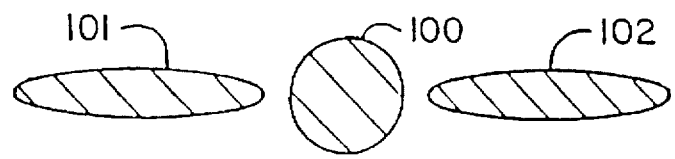
Figure 7:
Figure 8:
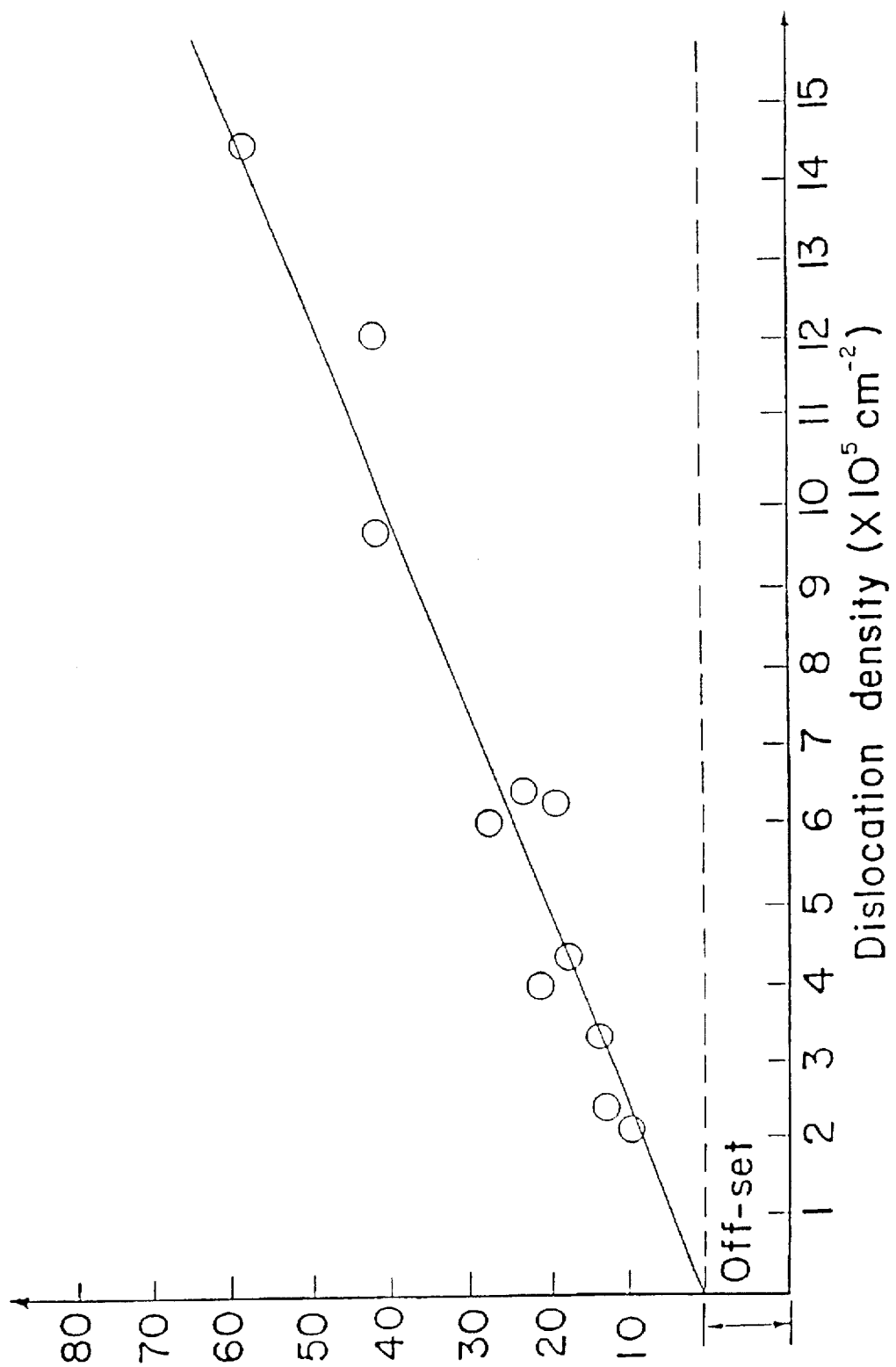
Figure 9:
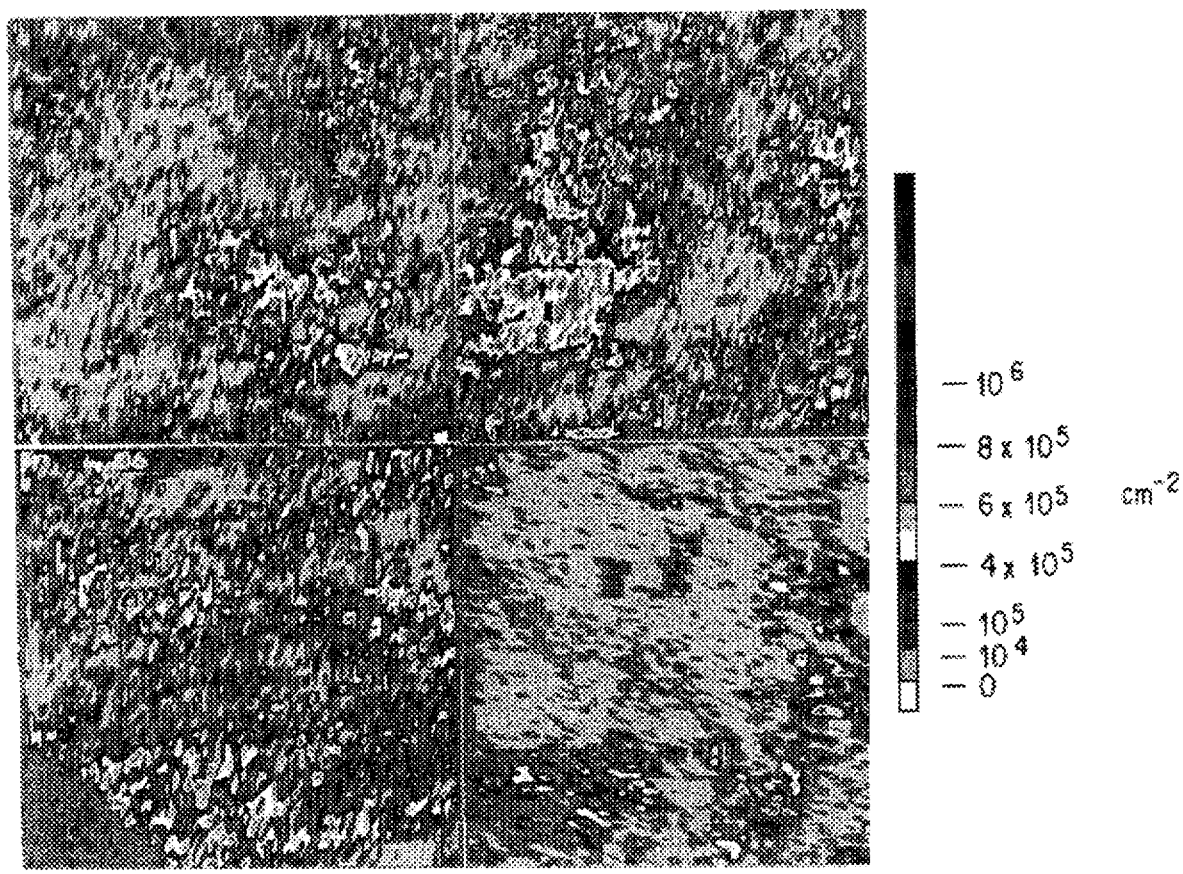
Figure 10B:
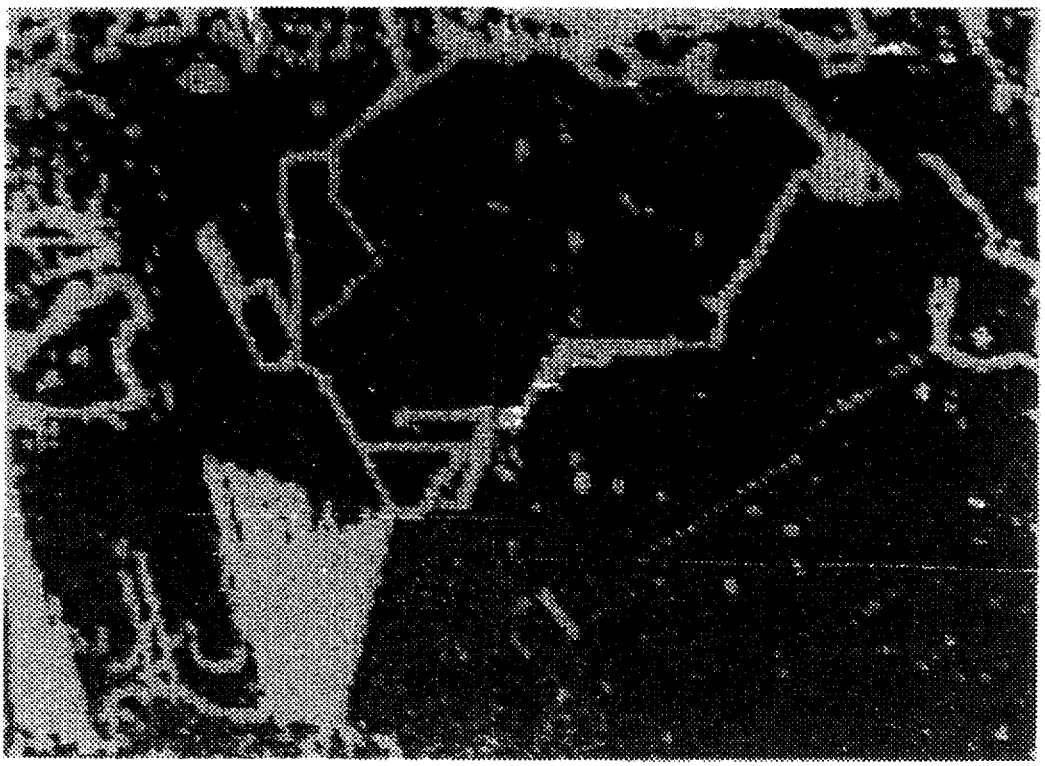
Figure 10A:
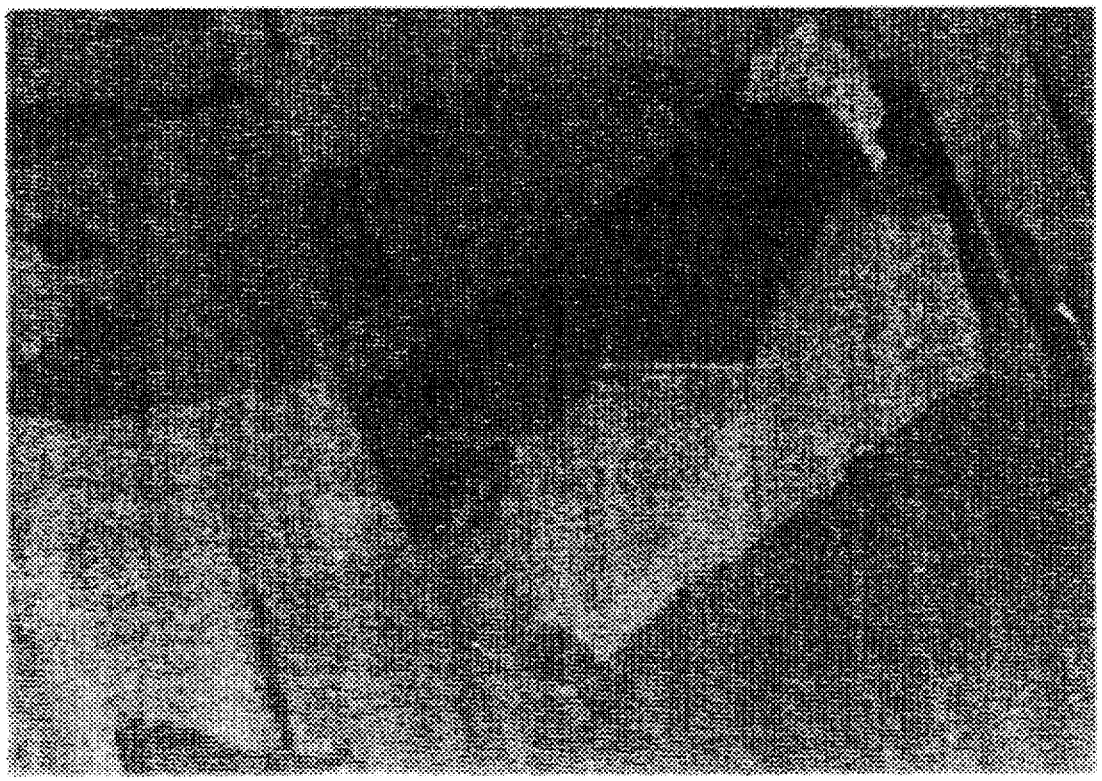
Figure 11:
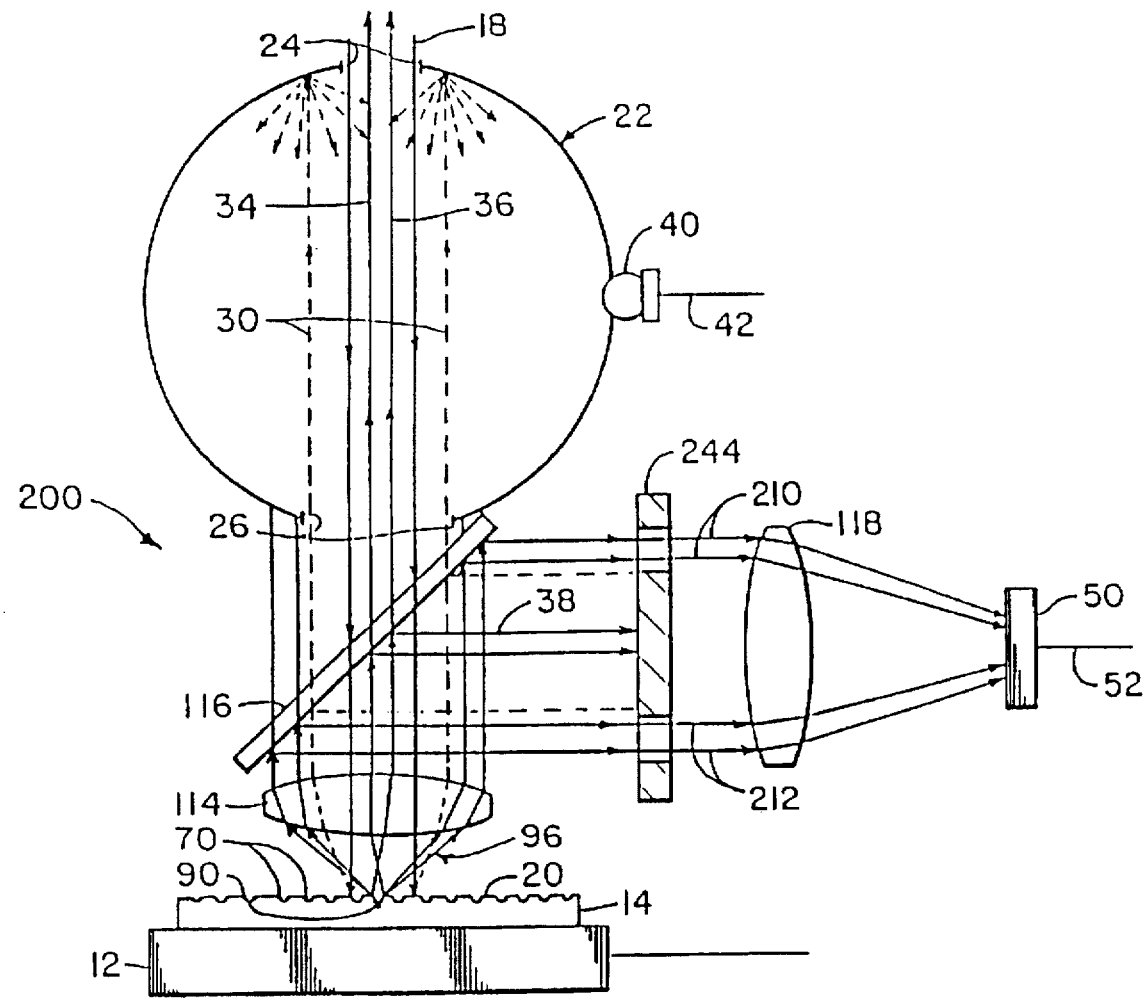
Figure 12:
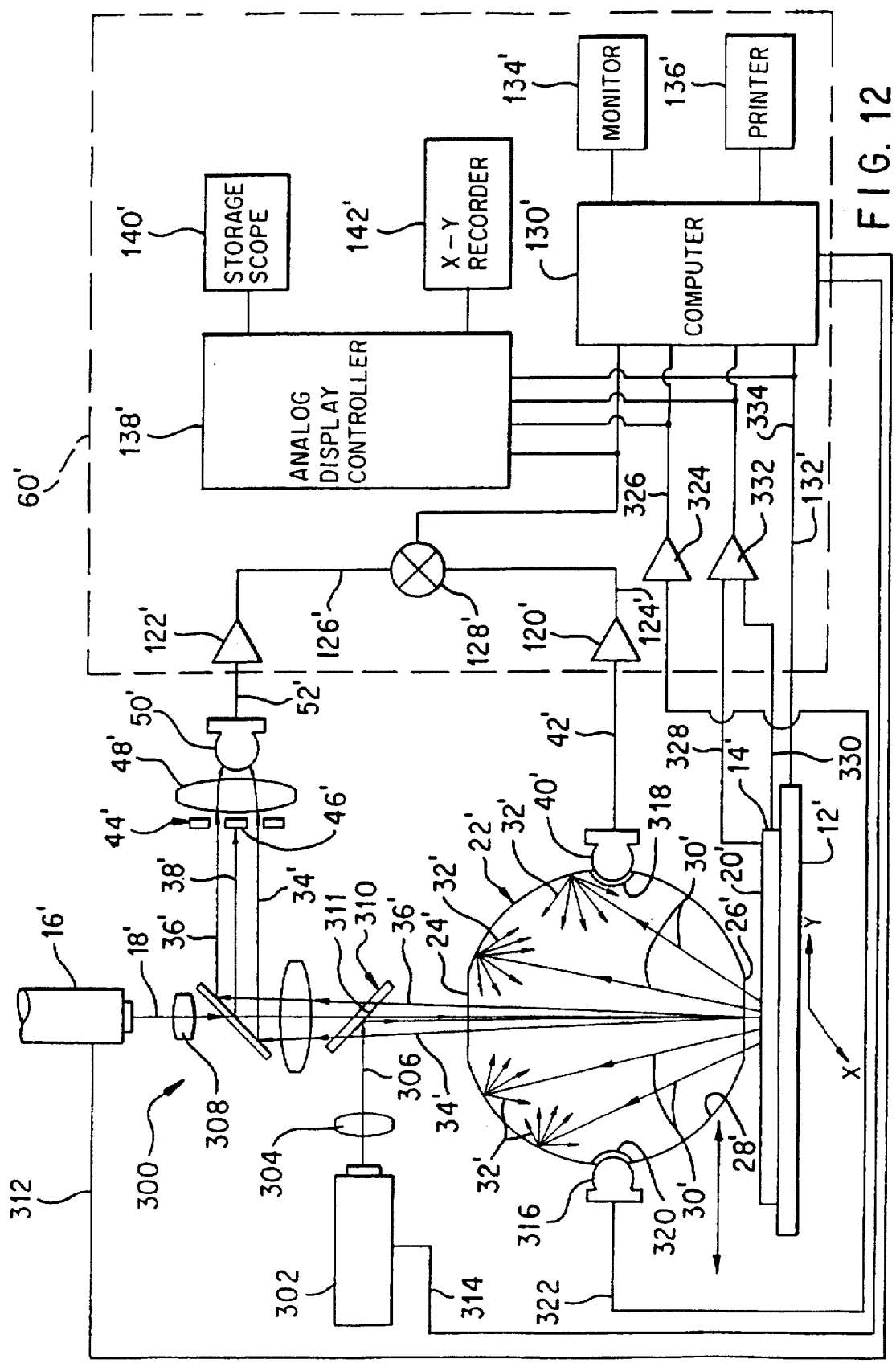
Figure 13:
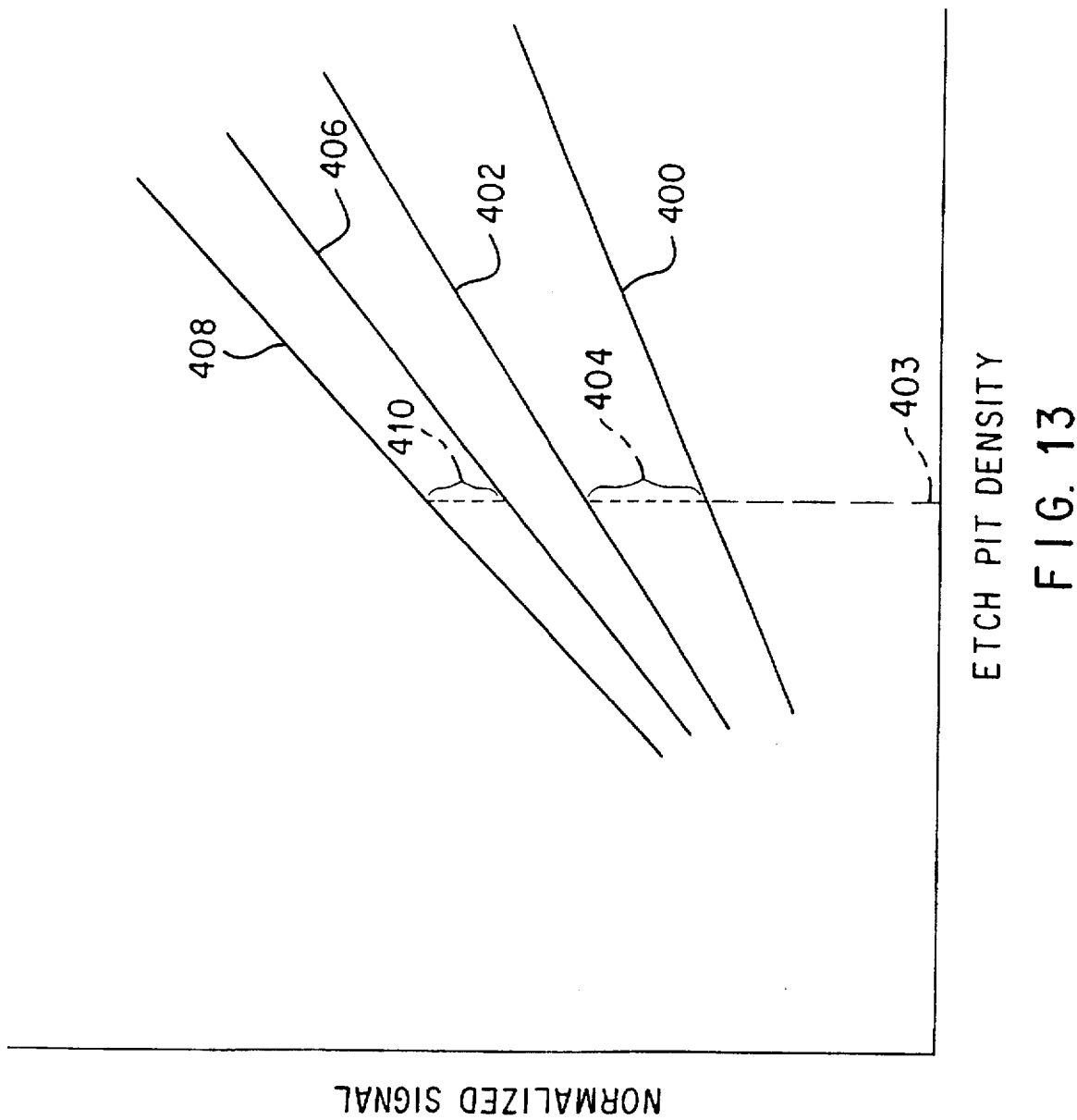
Figure 14:
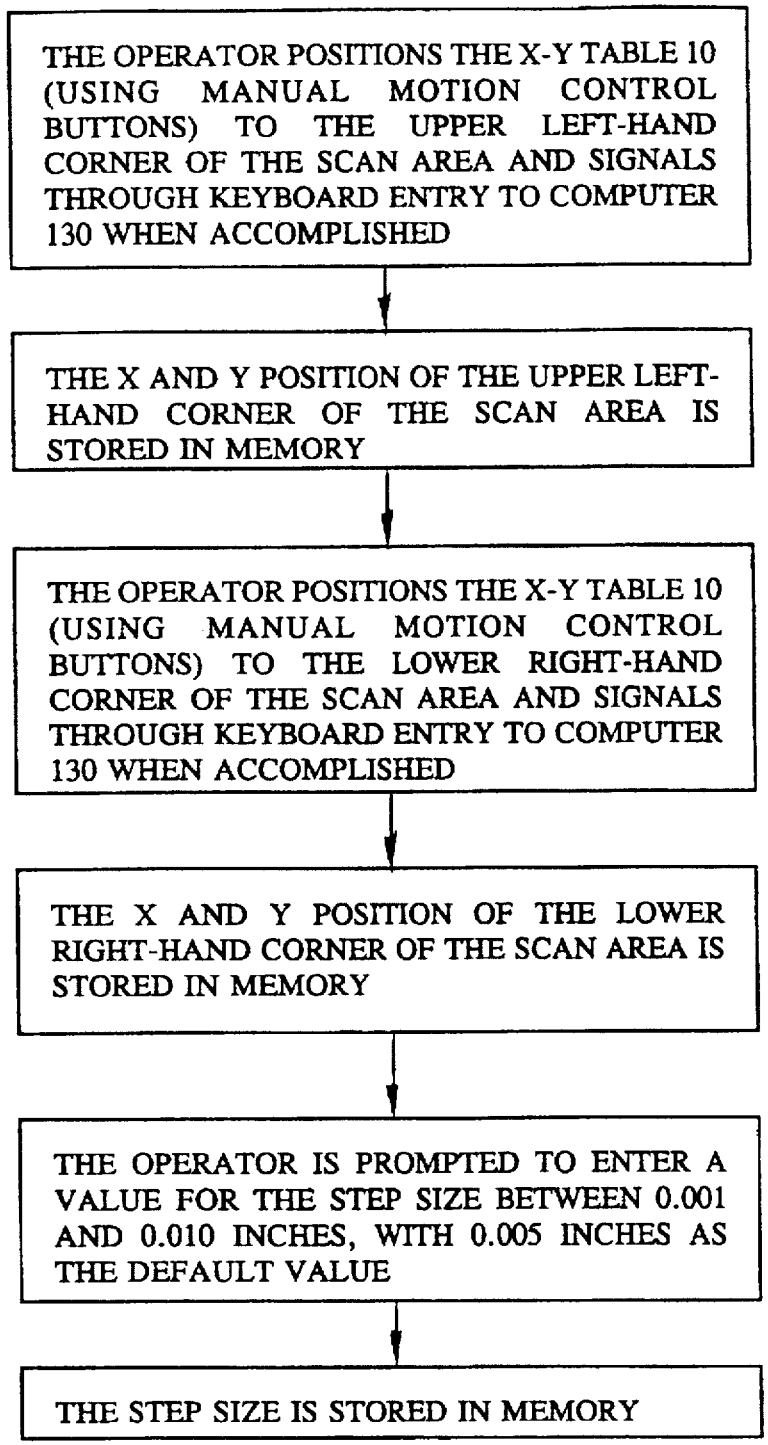
Figure 15:
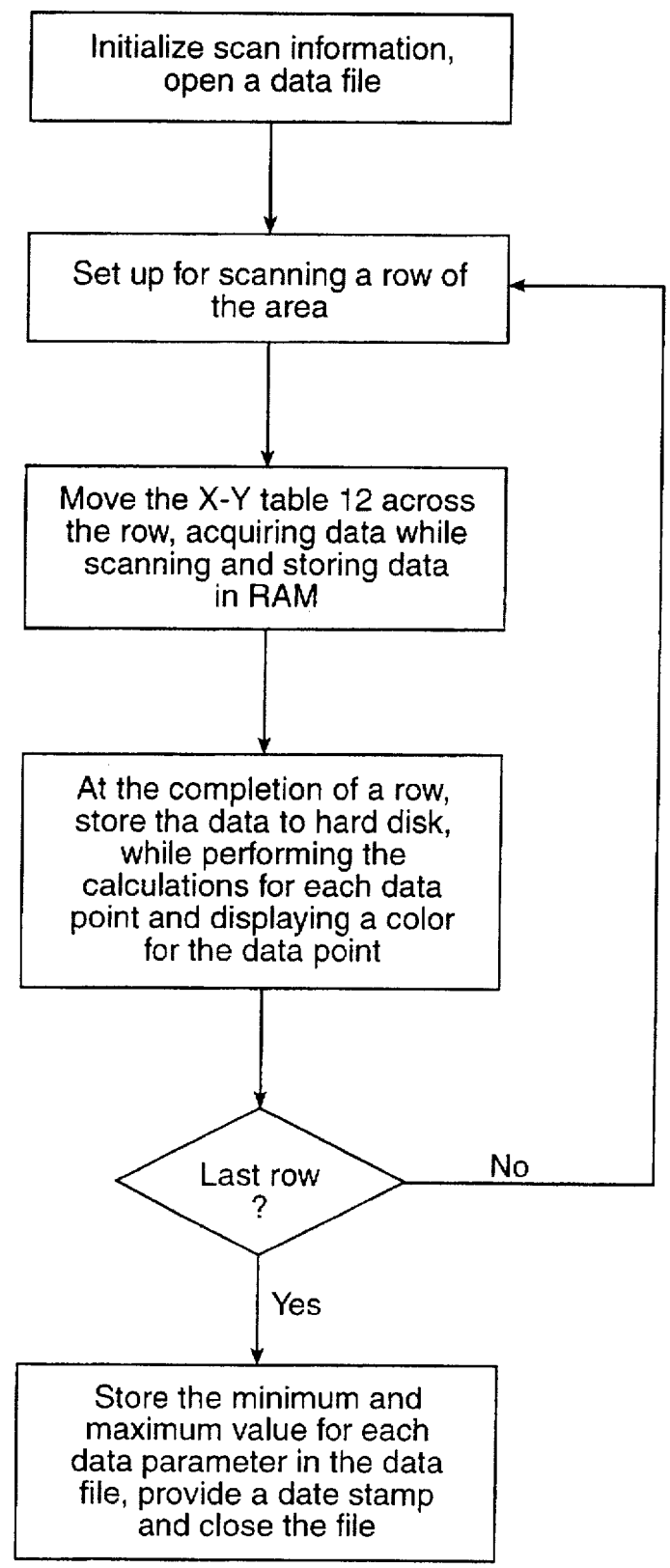
Figure 16:
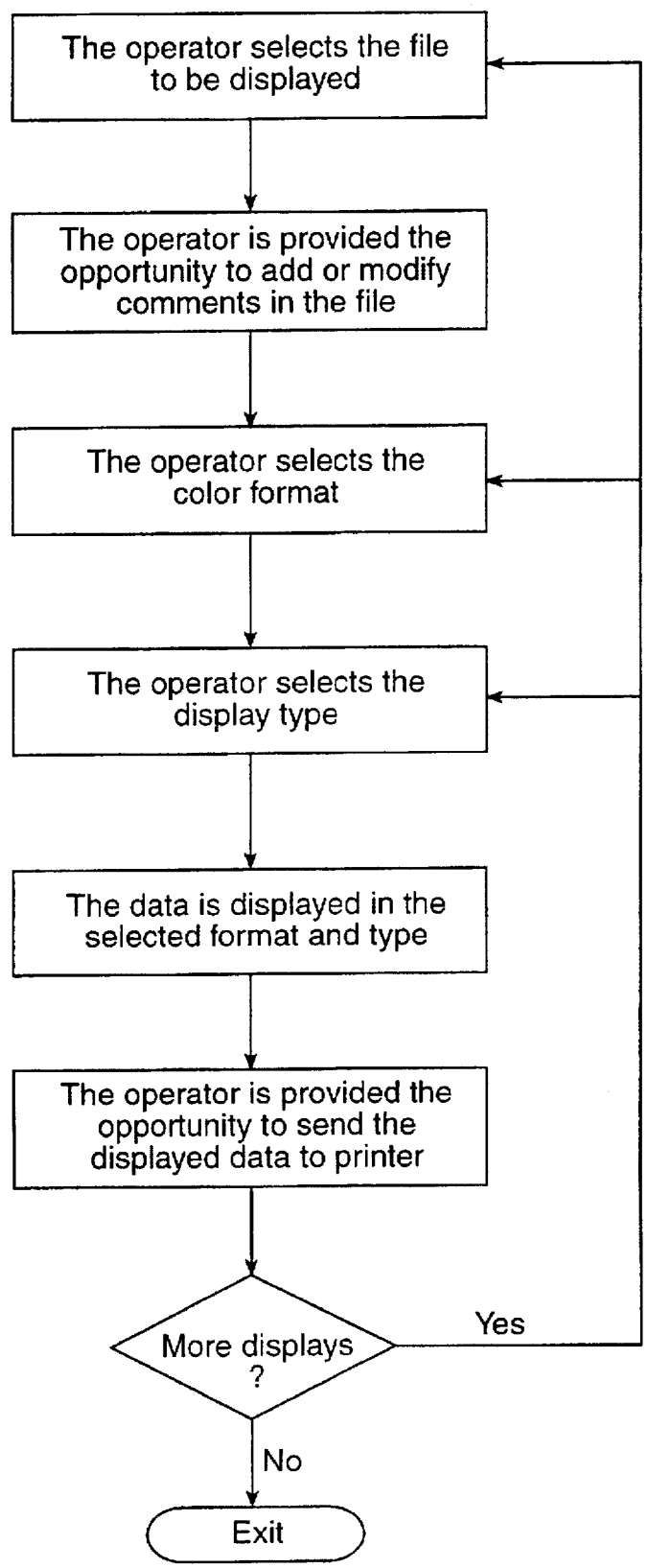
Figure 17:
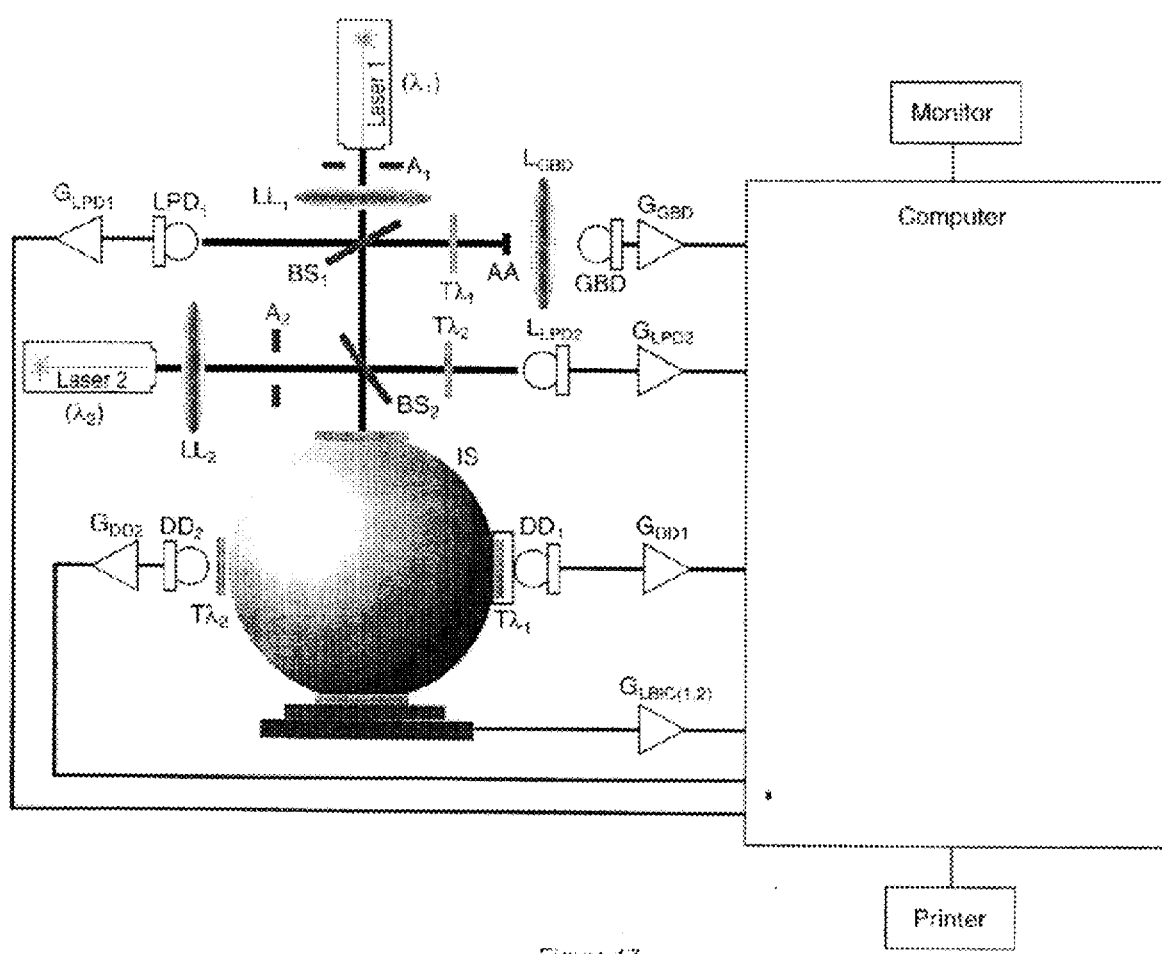
Figure 18:
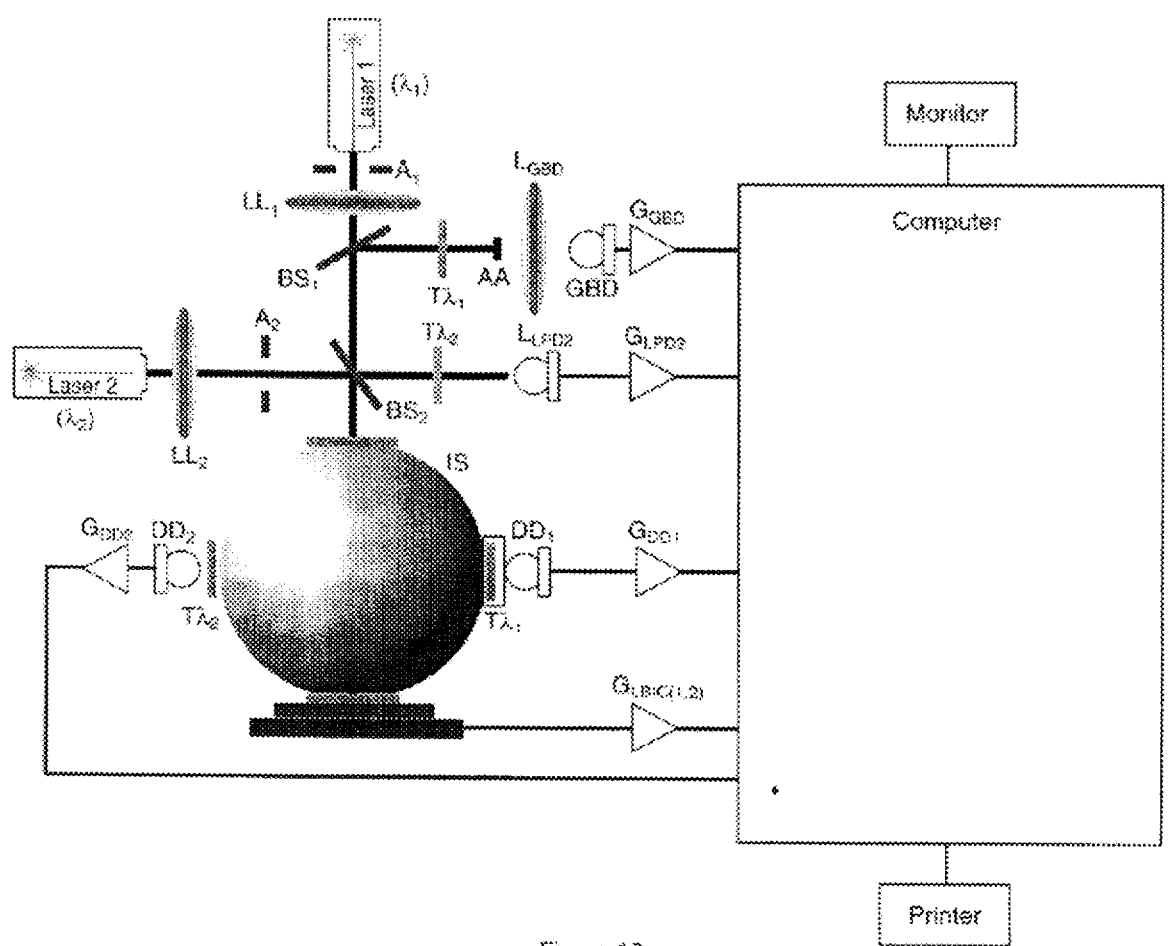
Figure 19:
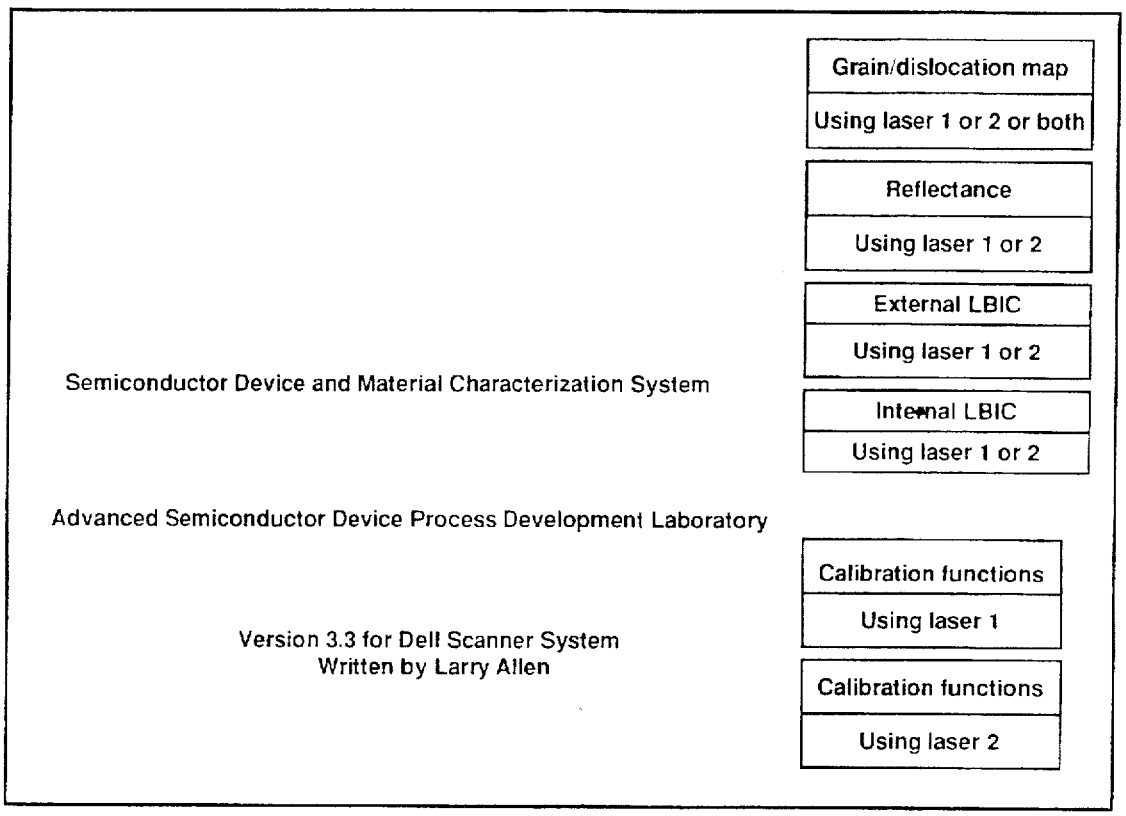
Figure 20:
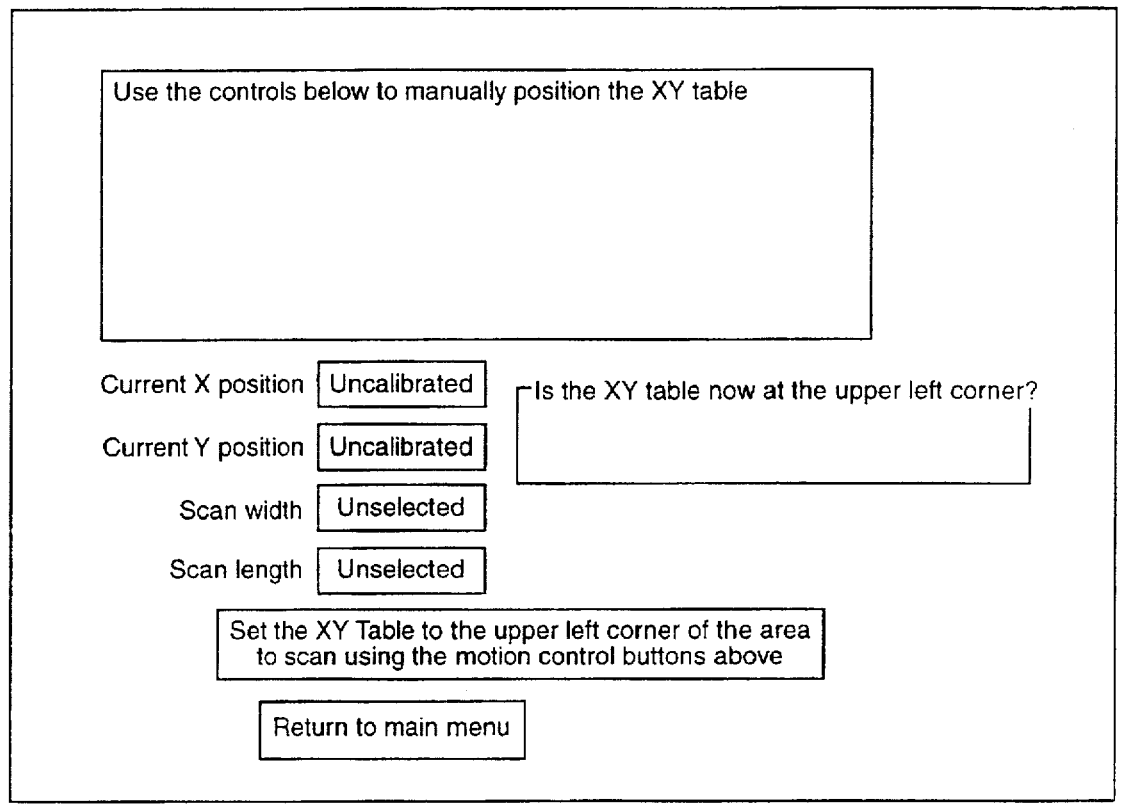
Figure 22:
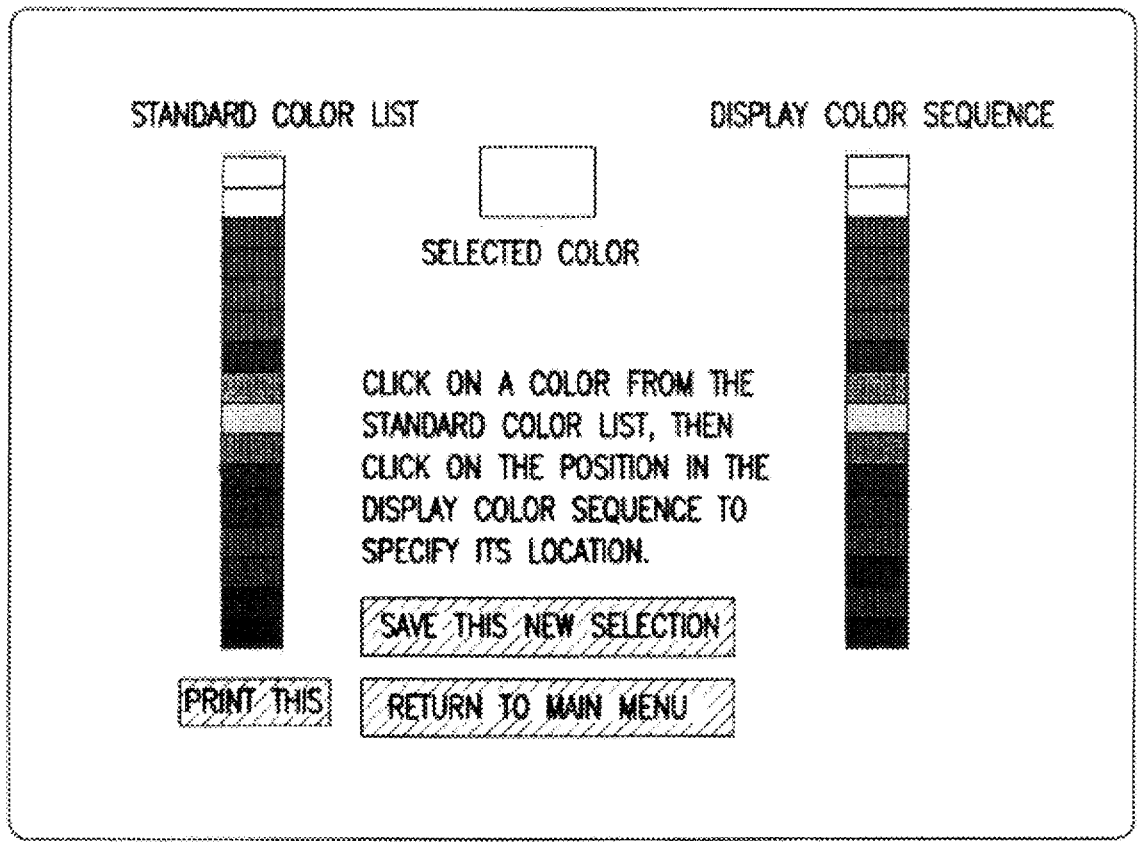
Figure 25:
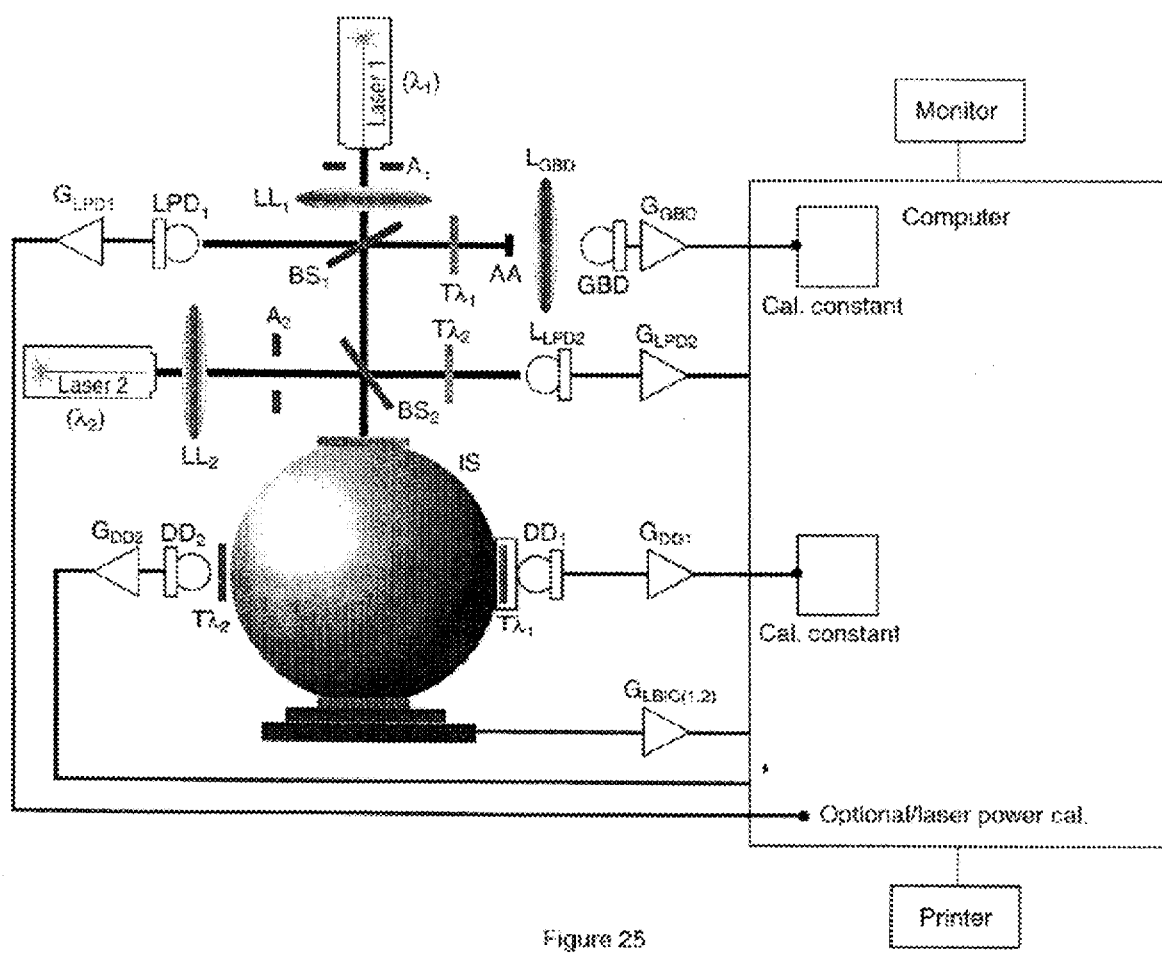
Figure 26:
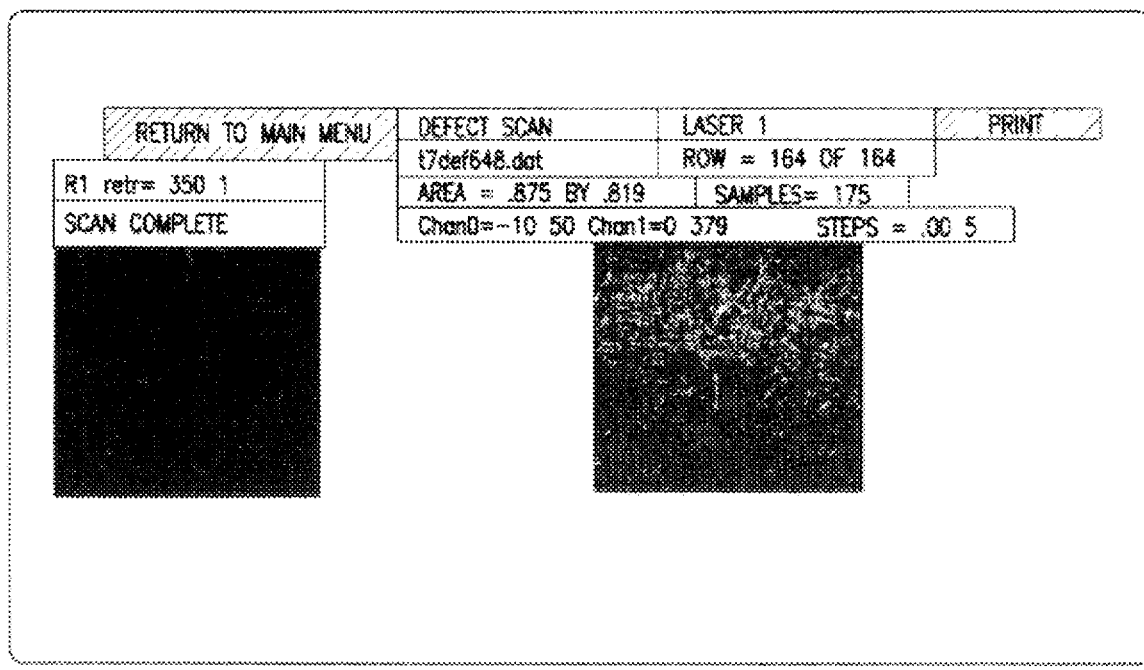
Figure 27:
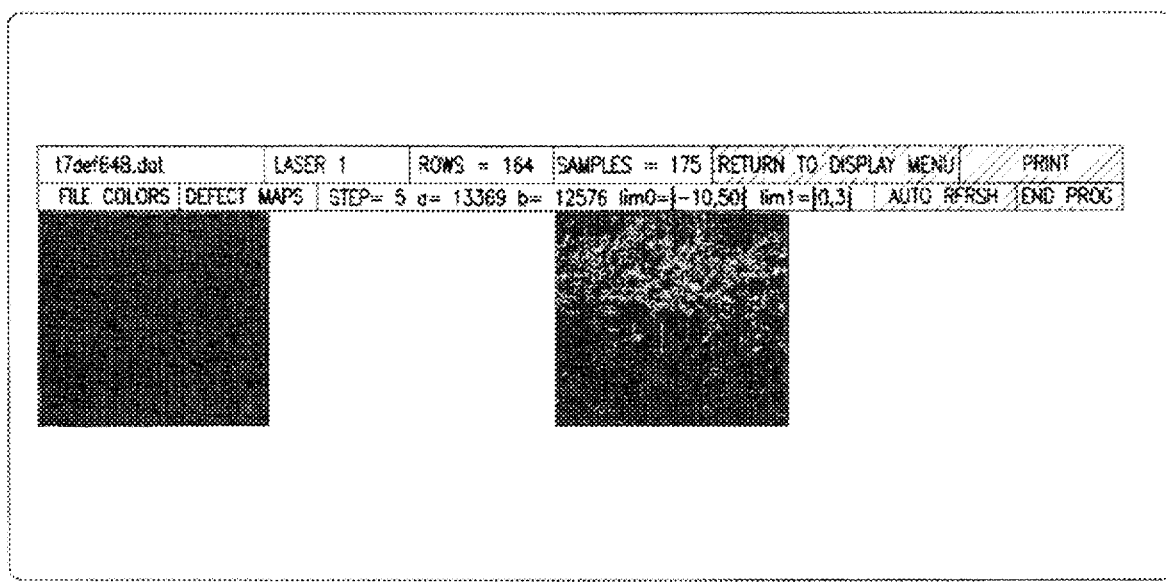
Figure 28:
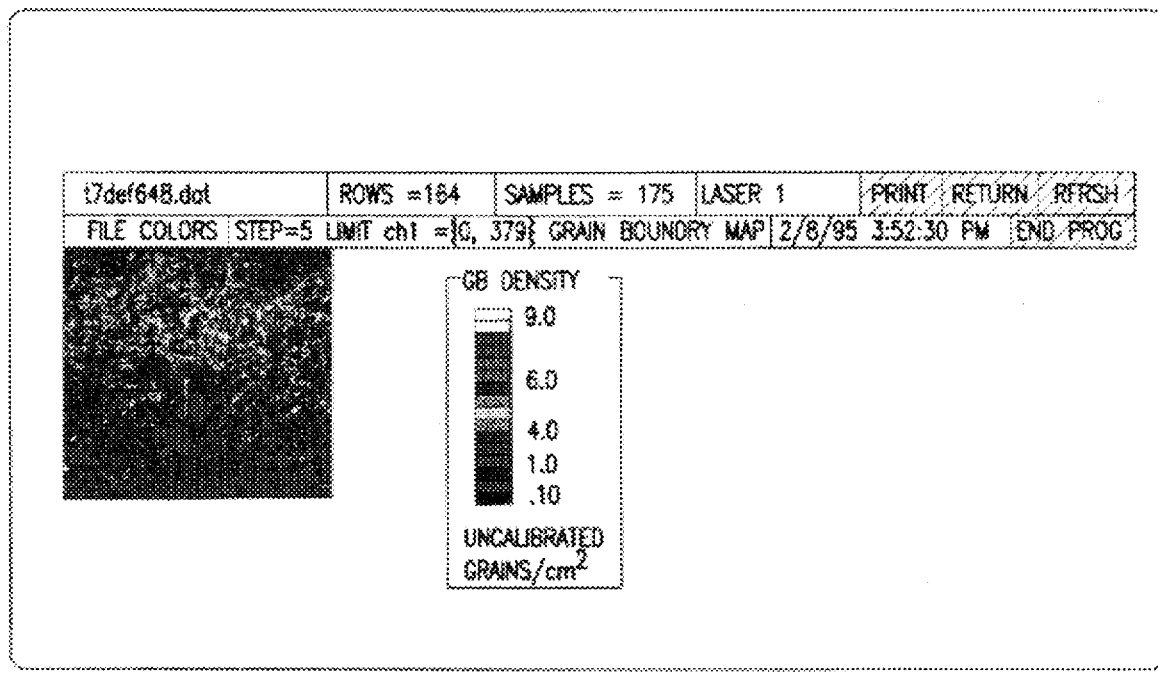
Figure 29:
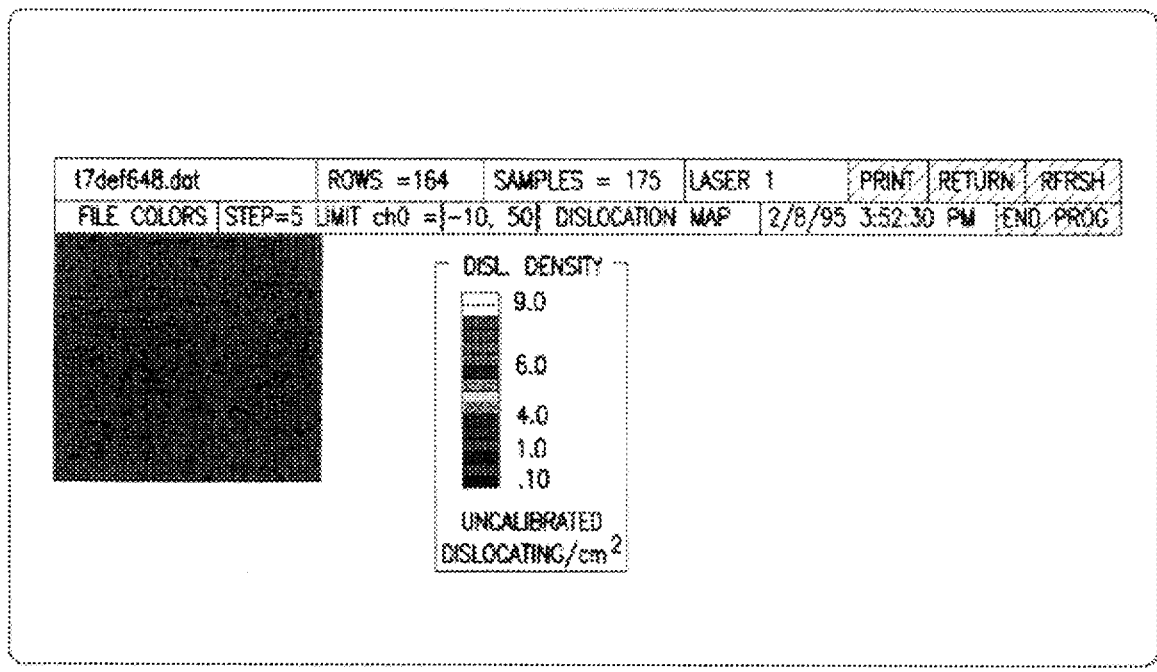
Figure 30:
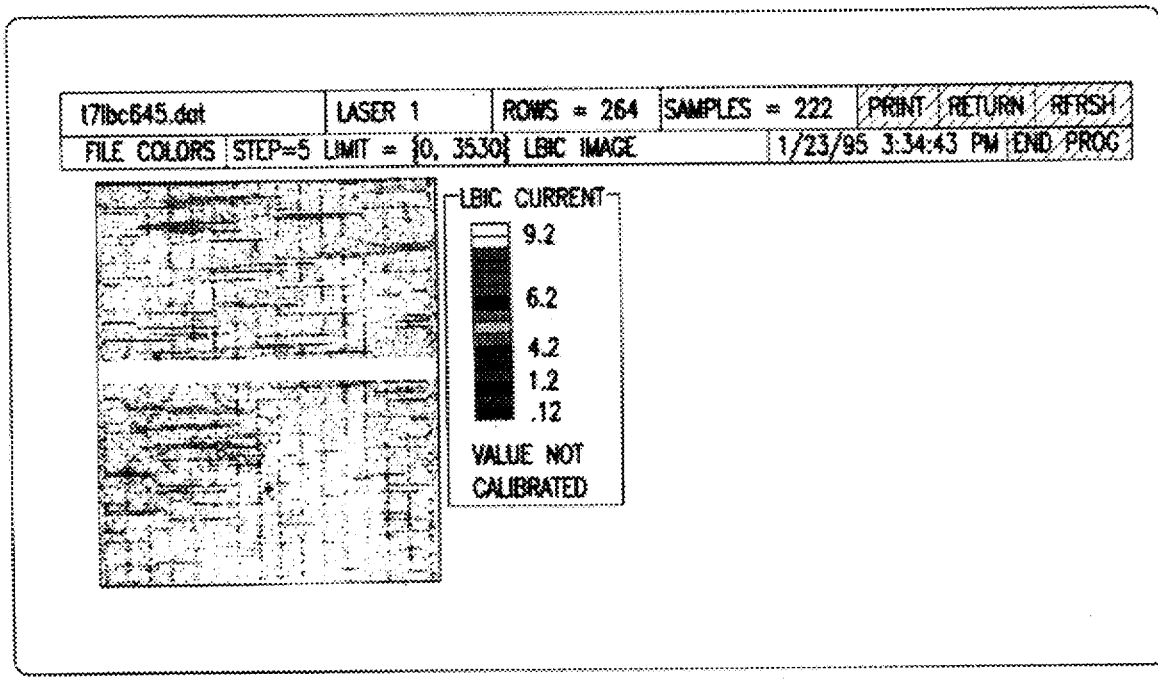
Figure 31:
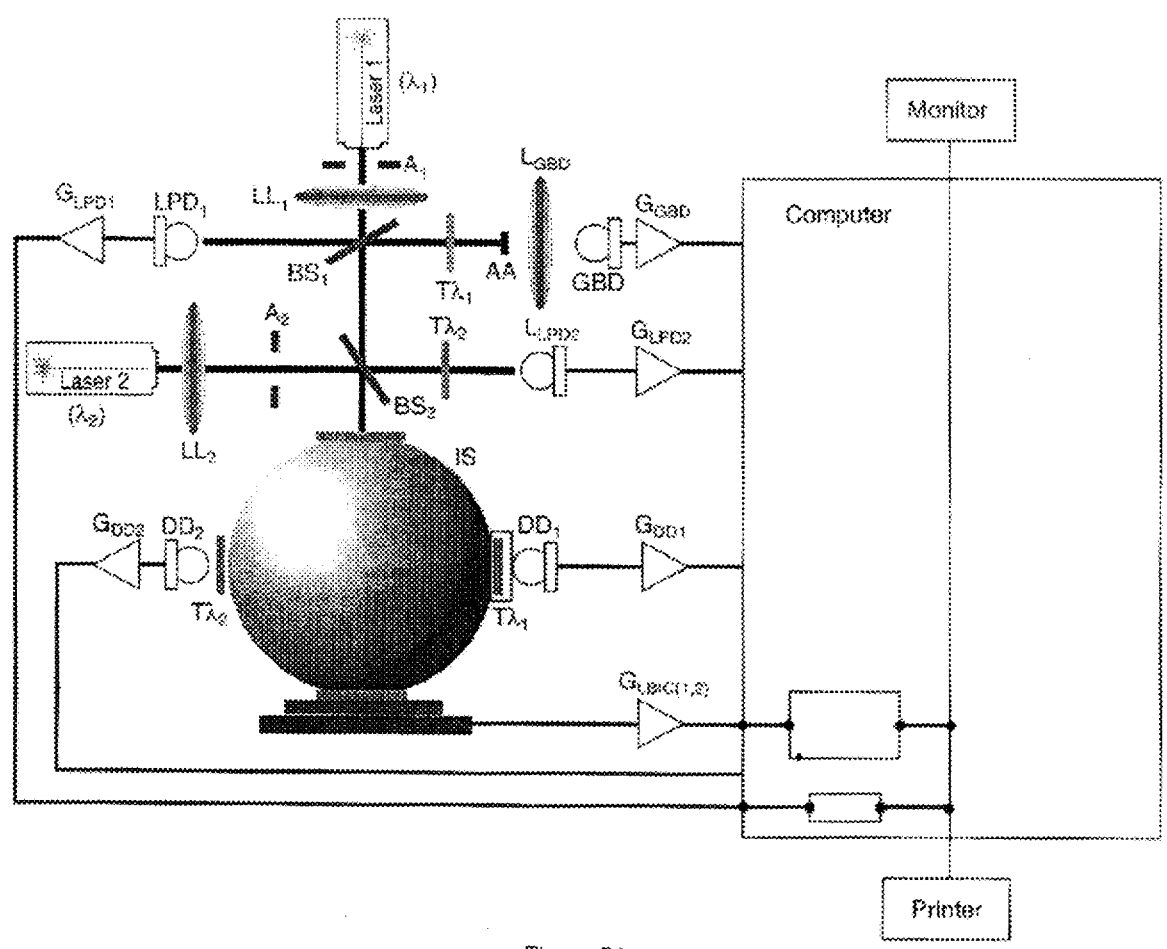
Figure 32:
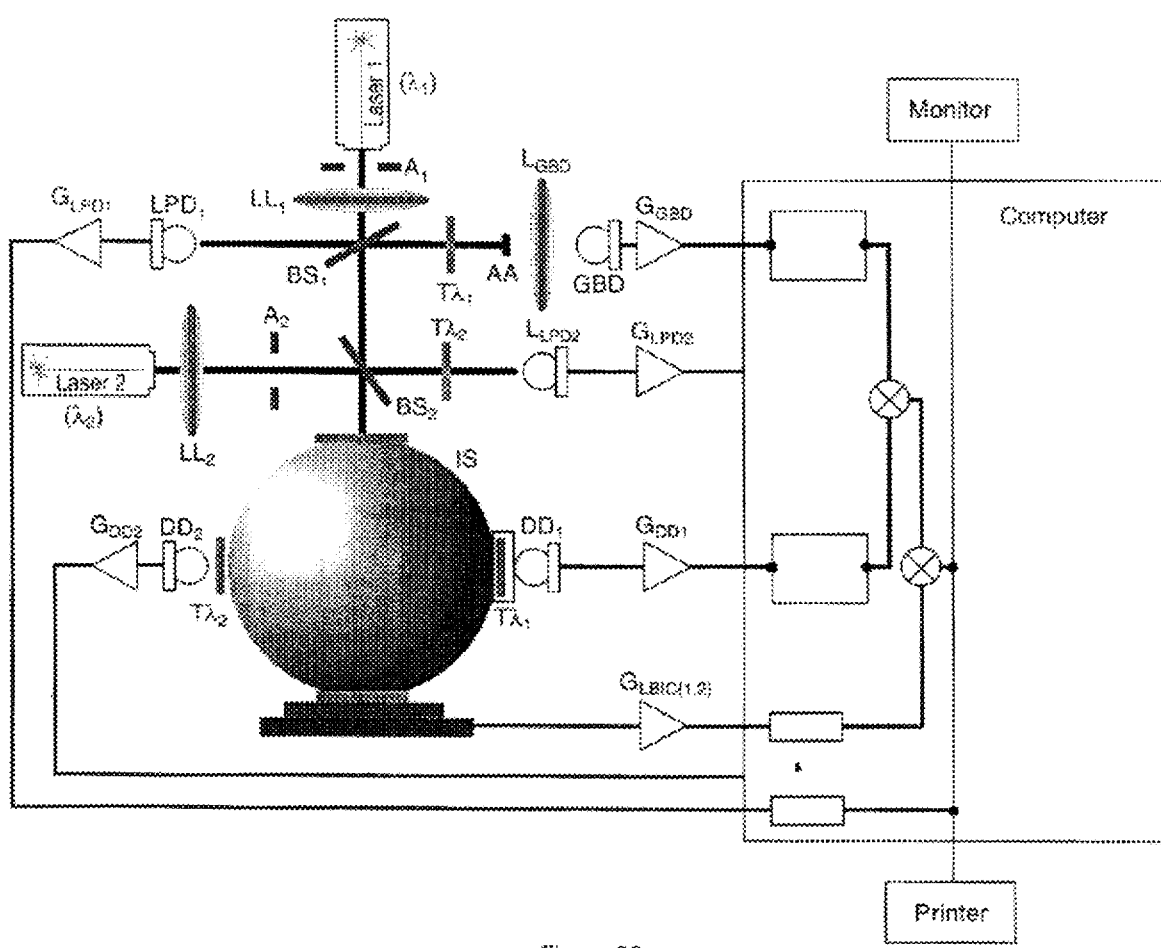
Figure 33:
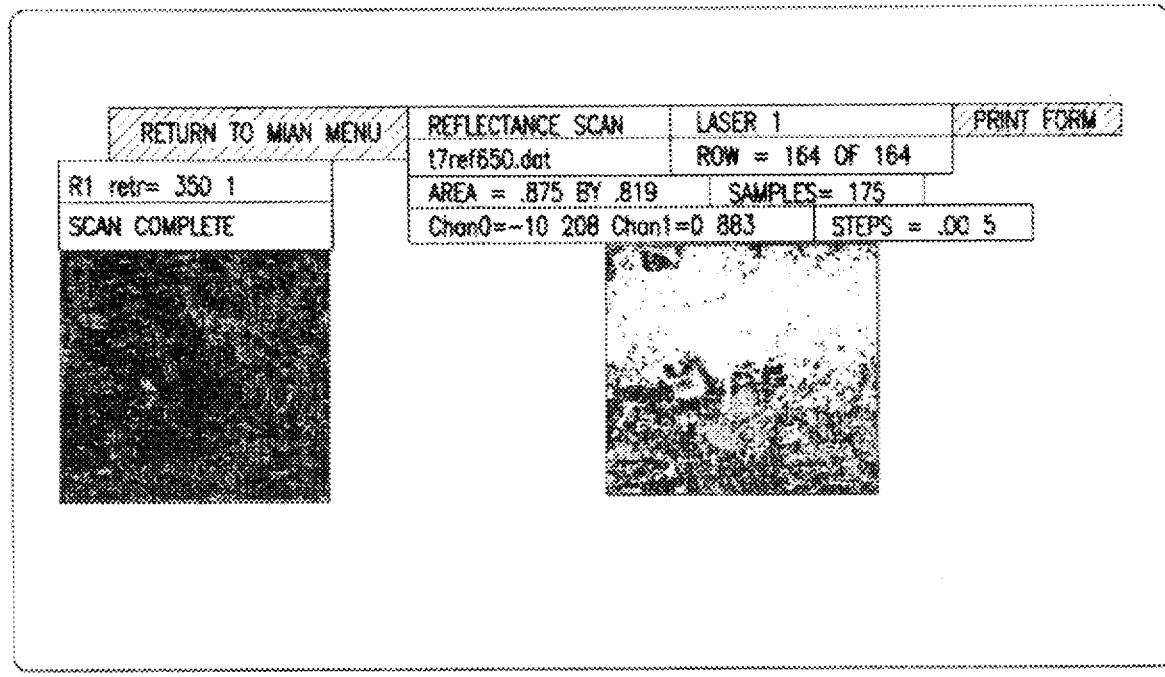
Figure 34:
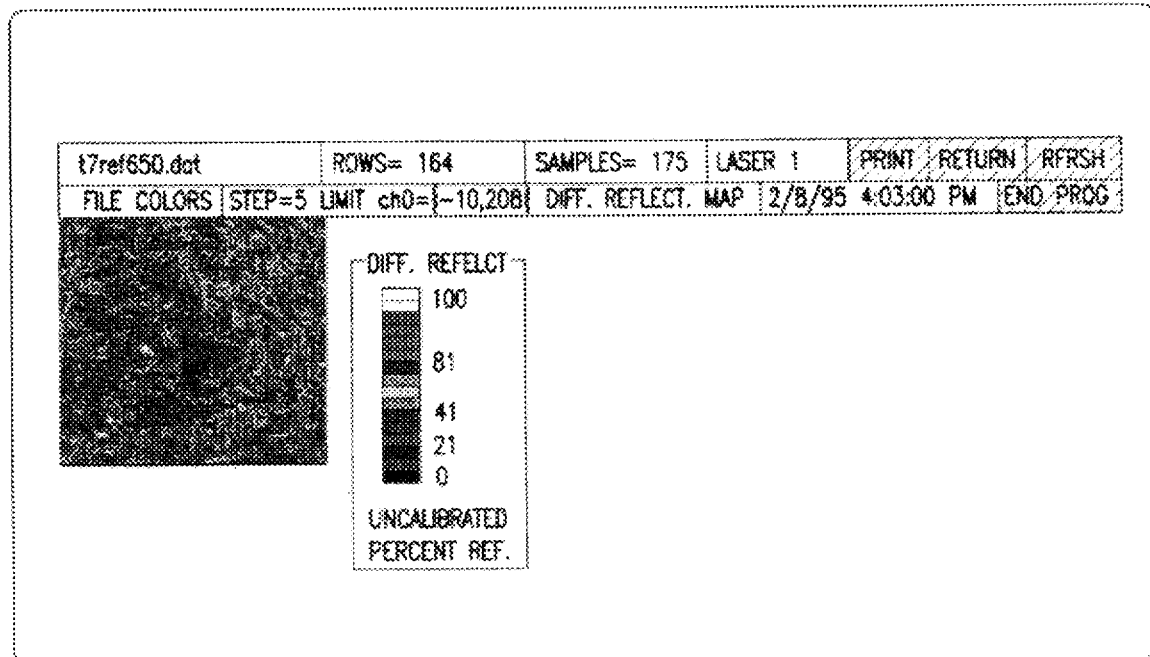
Figure 35:
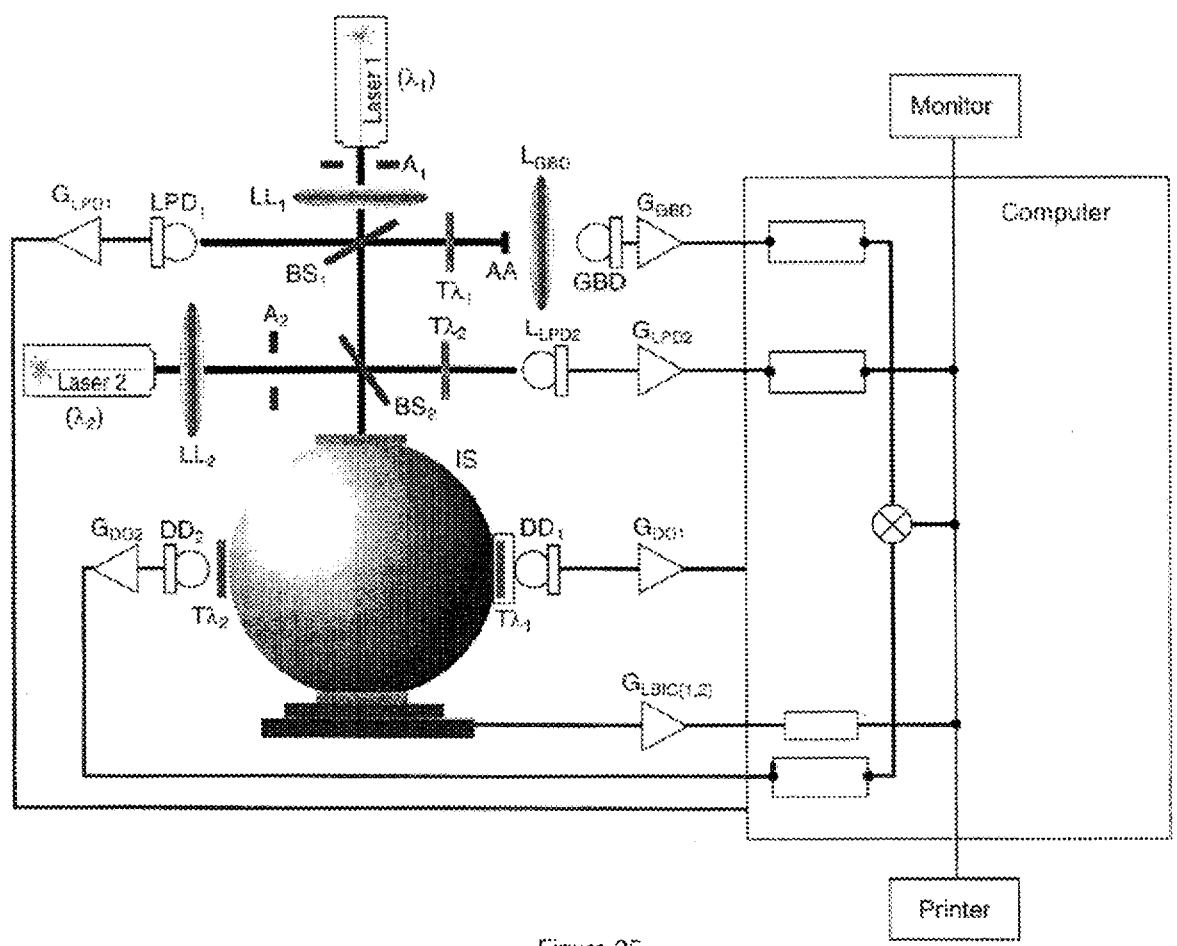

FIG. 4b is an illustration of the pattern of light scattered by a V-shaped etch grain boundary of FIG. 4a;

FIG. 5 illustrates the grain boundary light pattern of FIG. 4b superimposed on the etch pit light pattern of FIG. 3b, which combination occurs when a beam illuminating an etch pit sample surface encounters an etch grain boundary, as illustrated in FIG. 2;

FIG. 6 is an illustration of the central part of the grain boundary scattered light pattern that is captured separate from the etch pit scattered light according to this invention;

FIG. 7 is an illustration of the grain boundary scattered light pattern of FIG. 6 after removal of the center spot and converging for incidence on a photodetector;

FIG. 8 is a graph of detector signal intensity (integrated scattered light) plotted versus dislocation density;

FIG. 9 is a dislocation defect map of a crystal system wafer produced according to this process;

FIG. 10a is a photograph showing the grain boundaries in a surface of a polycrystalline silicon wafer;

FIG. 10b is a grain boundary defect map of the wafer of FIG. 10a produced according to this invention;

FIG. 11 is a schematic diagram of a second embodiment of a defect mapping system according to the present invention;

FIG. 12 is a schematic diagram of a third embodiment of a defect mapping system and a light beam induced current mapping system according to the present invention;

FIG. 13 is a graphical representation of the relationship between the normalized signal received from the diffuse light reflected from the material as a function of etch pit density at different wavelengths and for different etch pit sizes;

FIG. 14 is a flow chart illustrating the flow of operations performed by the operator and system, with the aid of the software in the computer;

FIG. 15 is a flow chart illustrating the flow of operations performed by the operator and system, with the aid of the software in the computer;

FIG. 16 is a flow chart illustrating the flow of operations performed by the operator and system, with the aid of the software in the computer;

FIG. 17 is a schematic diagram of a fourth embodiment of a defect mapping system and a light beam induced current mapping system according to the present invention in which the laser power can be monitored;

FIG. 18 is a schematic diagram of the fourth embodiment of FIG. 17 shown in a different operational mode in which the laser power can be monitored in an alternative fashion;

FIG. 19 is an image displayed on the computer monitor illustrating how the operator can select one of several different functions;

FIG. 20 is an image displayed on the computer monitor illustrating the control provided to manually position the X-Y table during the setup operation;

FIG. 21 is an image displayed on the computer monitor illustrating the control provided for selecting the step size;

FIG. 22 is an image displayed on the computer monitor illustrating the control provided to select a color sequence;

FIG. 23 is an image displayed on the computer monitor illustrating the selection of the dynamic range of the data displayed;

FIG. 24 is an image displayed on the computer monitor illustrating the selection of the laser used in measuring the relevant characteristics;

FIG. 25 is a schematic diagram of the fourth embodiment showing the components arranged to measure dislocation density and grain boundary maps simultaneously;

FIG. 26 is an image displayed on the computer monitor during simultaneous generation of dislocation density and grain boundary maps;

FIG. 27 is a display of a stored image file on the computer monitor corresponding to dislocation density and grain boundary maps of a piece of semiconductor material;

FIG. 28 is an image corresponding to a grain boundary map alone, displayed on the computer monitor, illustrating capability to separate a single image from stored data for a pair of images of FIG. 27;

FIG. 29 is an image corresponding to a dislocation density map alone, displayed on the computer monitor, illustrating capability to separate a single image from stored data for a pair of images of FIG. 27;

FIG. 30 is an image displayed on the computer monitor illustrating an external LBIC map of a solar cell;

FIG. 31 is the schematic diagram of the fourth embodiment showing the components arranged to measure external LBIC response;

FIG. 32 is the schematic diagram of the fourth embodiment showing the components arranged to measure internal LBIC response;

FIG. 33 is an image displayed on the computer monitor showing a diffuse reflectance and specular reflectance map of the sample of semiconductor material;

FIG. 34 is an image displayed on the computer monitor showing a diffuse reflectance map of the sample of semiconductor material; and FIG. 35 is the schematic diagram of the fourth embodiment showing the components arranged to measure internal LBIC response with Laser2 corresponding to the minority carrier diffusion length map.

DETAILED DESCRIPTION OF THE PREFERRED EMBODIMENTS

Figure 1:
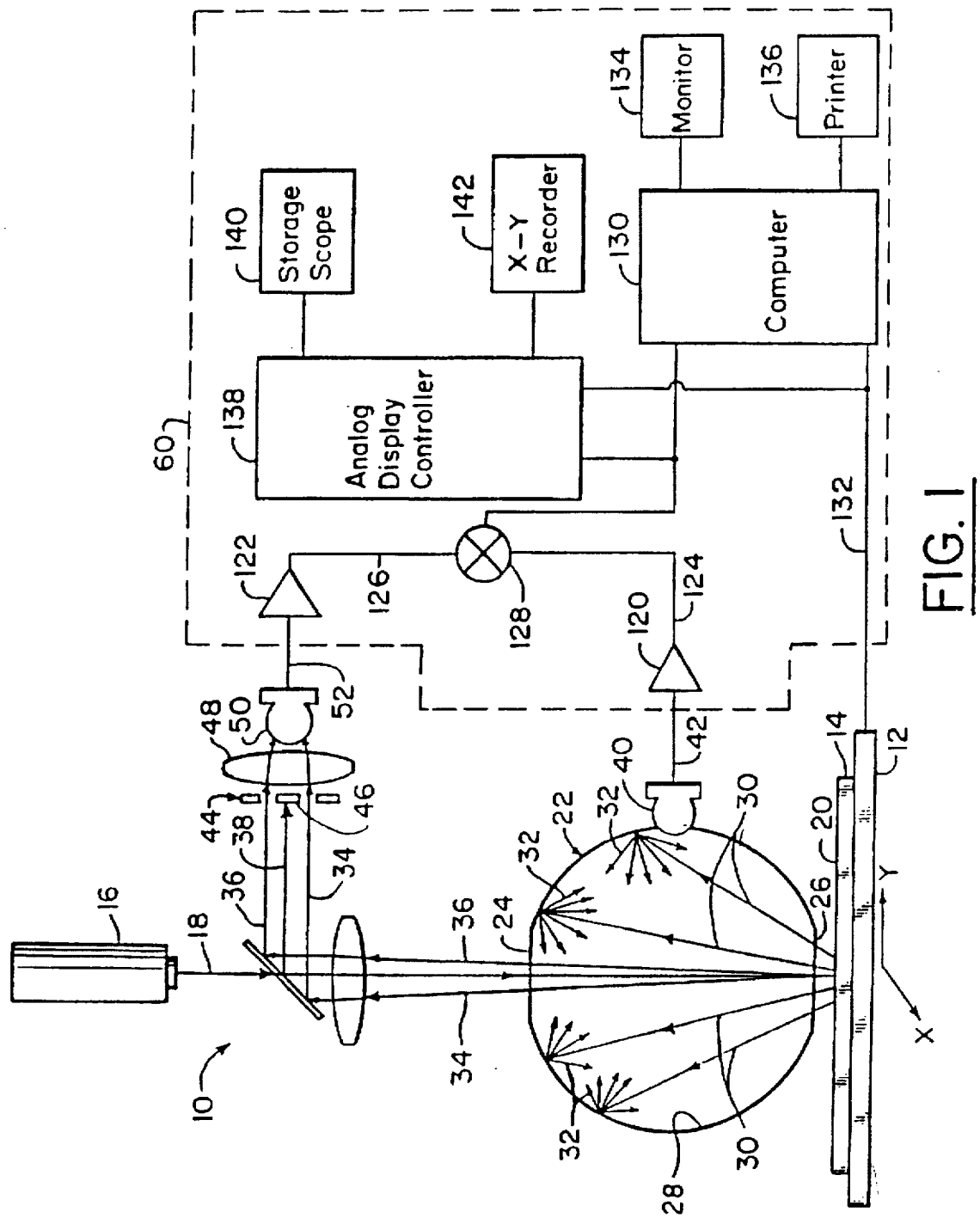

The improved defect mapping system 10 of this invention is illustrated schematically in FIG. 1. An X-Y translation stage or table 12 is provided for supporting a crystalline sample or substrate 14 positioned for defect detection and mapping according to this invention. A laser beam generator 16, such as a HeNe laser system capable of generating a laser beam 18 of light with a wavelength of approximately 6.328 Å, is positioned above the stage 12 and preferably oriented to direct a laser beam 18 perpendicularly onto the exposed surface 20 of crystalline material or sample 14.

A light integrating sphere 22, has two diametrically opposed apertures 24, 26 positioned to allow transmission of the laser beam 18 through the light integrating sphere 22, when it is positioned between the laser generator 16 and the sample 14. However, the light integrating sphere 22 captures light rays 30 that are scattered by the surface 20 of sample 14 through the bottom aperture 26. The interior surface 28 of the integrator 22 is coated with a material, such as magnesium oxide, that enhances uniform scattering and integrated distribution or diffusion of light rays 30 captured therein through the bottom aperture 26, as illustrated at 32. A first photodetector 40 positioned in the side of the light integrating sphere 22 detects the intensity of diffused light 32 in the light integrating sphere 22 and produces an analog signal on lead 42 indicative of the diffused light 32 intensity. As illustrated in the graph in FIG. 8, and as will be discussed in more detail below, the intensity of the diffused or integrated scattered light 32 in FIG. 1, thus the amplitude of the signal produced on lead 42, is a direct measure of etched pit dislocation density (EPD) on the position of surface 20 of sample 14 that is illuminated by laser beam 18.

At the same time, the near specular components 34, 36 of light scattered by etched grain boundaries (not shown in FIG. 1, but described below) in the surface 20 of a polycrystalline sample 14, along with specular light component 38, are allowed by bottom aperture 26 and top aperture 24 to pass through the light integrating sphere 22, as illustrated in FIG. 1. The specular light component 38, which is primary comprised of light reflected by smooth portions, i.e., non-defect portions, of the surface 20 of sample 14, is blocked and eliminated by an opaque center 46 of a center blocking aperture 44, while the near specular light components 34, 36 are passed to a convex converging lens 48 and to a second photodetector 50. Since most of the light that reaches this second photodetector 50 is the near specular component of light scattered by etched grain boundaries, as will be described in more detail below, a strong electric signal produced on lead 52 by photodetector 50 indicates the presence of a grain boundary in the portion of the surface 20 of sample 14 that is illuminated by the laser beam 18.

The signal processing and control unit 60 shown in FIG. 1 processes and stores the signals from the photodetectors 40 and 50 in conjunction with X-Y position information of the stage 12, as the stage 12 rasters the sample 14 under the laser beam 18. Therefore, visual displays or other outputs of etch pit density (EPD) or grain boundary mapping can be produced for all or any desired portion of the surface 20 of sample 14.

Figure 3A:
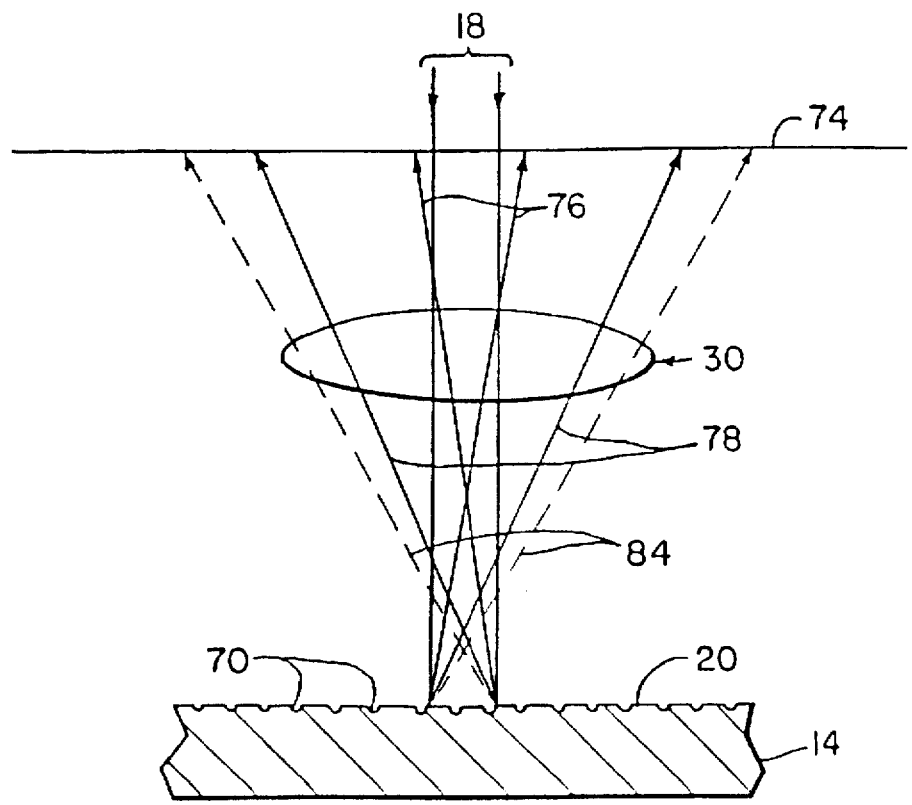

Referring now to FIGS. 3a and 3b, a crystalline sample 14 with etch pits 70 in the surface 20 where dislocation defects occur is shown illuminated by a laser beam 18. When properly etched, as will be described in more detail below, the etch pits 70 scatter the light in a definite and repeatable pattern 72 illustrated in FIG. 3b. The pattern 72 in FIG. 3b is the projection of the scattered light beams in FIG. 3a on the plane 74. Essentially, the etch pits 70 scatter most of the incident light from beam 18 in a conical pattern, as show in FIG. 3a, between about five degrees (5°) and twenty degrees (20°) from normal. The beams 76 illustrate the inner boundary of this range, and the beams 78 illustrate the outer boundary. Corresponding boundaries 76 and 78 define the primary high intensity light ring 80 of the resulting pattern 72 in FIG. 3b. A fringe ring 82 of less intensity surrounds the primary ring 80, as depicted by scattered fringe rays 84. The center circle 73 of pattern 72 is essentially devoid of scattered light from the etch pitted surface 20. All of the scattered light in the primary ring 80 and the fringe ring 82 of pattern 72 is collectively designated as the etch pit scattered light 30 for convenience in describing this invention.

Figure 3D:
Figure 3C:
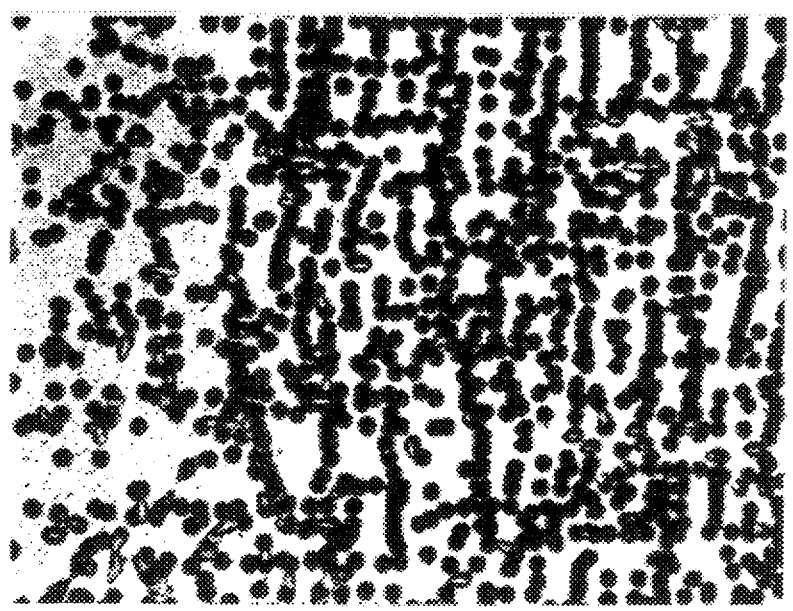
Figure 3F:
Figure 3E:
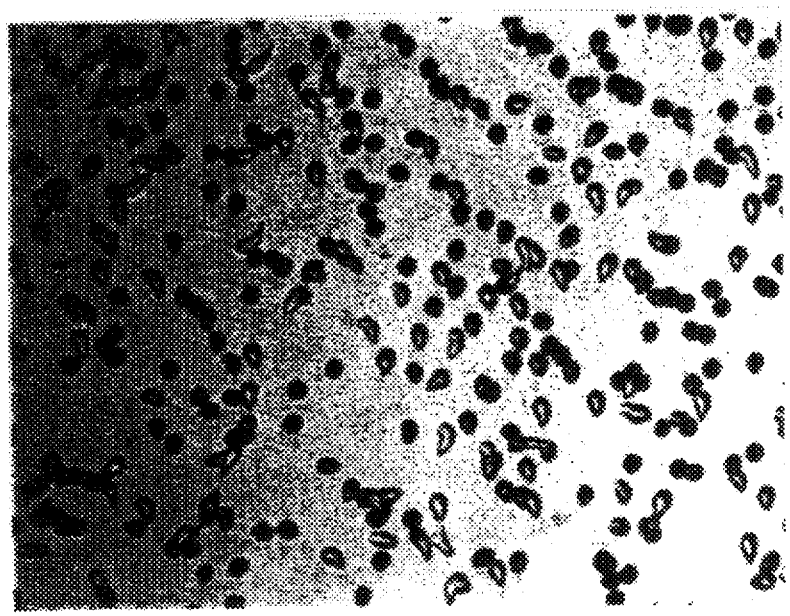
Figure 3H:
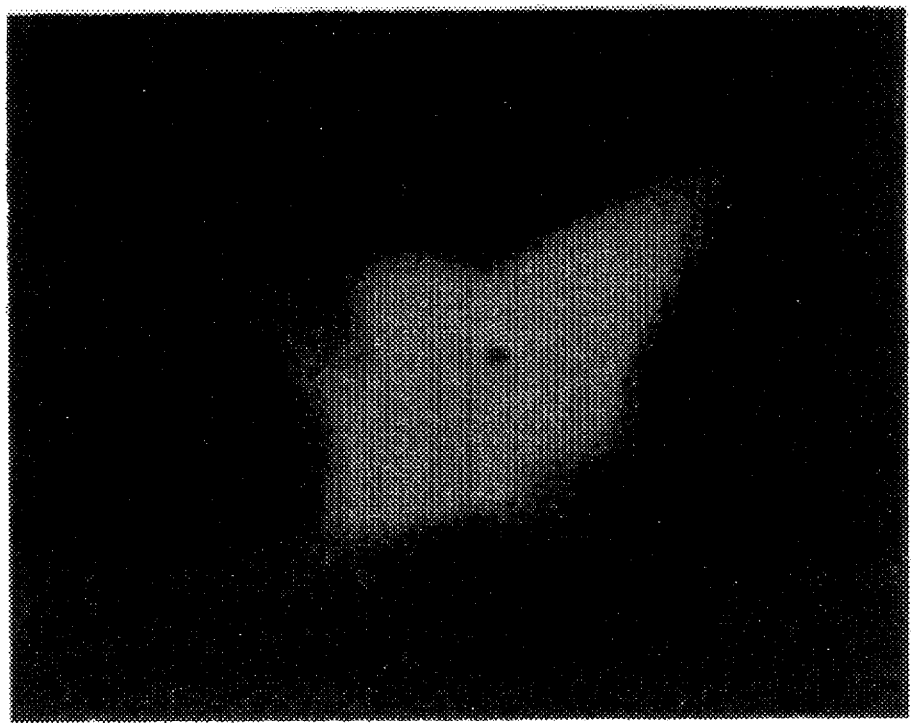
Figure 3G:
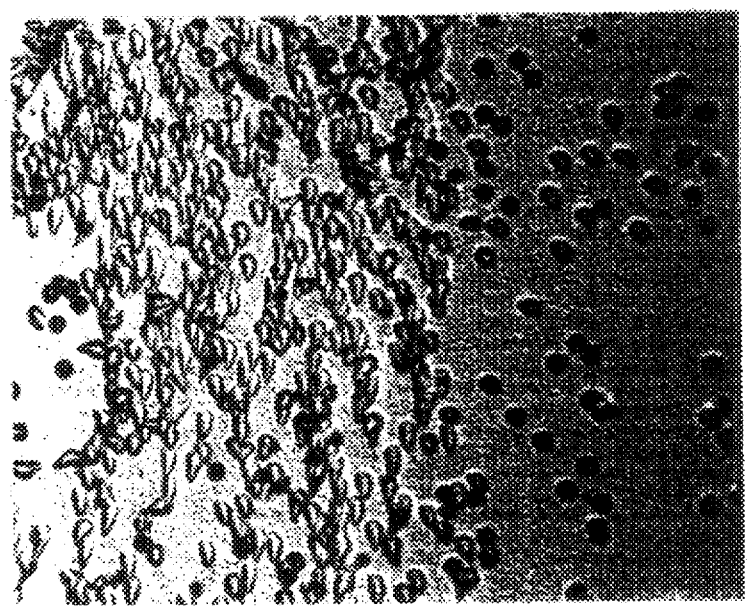

FIG. 3d is an illustration of a pattern 72 produced scattered light from the substantially circular shaped etch pits in FIG. 3c. Such circular shaped etch pits indicate dislocation defects that are oriented substantially normal to the surface, and, when etched as described below for this invention, will always produce the characteristic circular pattern of etch pit scattered light shown in FIG. 3d and depicted in FIG. 3b. In contrast, dislocation defects that are oriented oblique to the surface produce elliptical shaped etch pits, as shown in FIG. 3e. Such elliptical etch pits produce an elliptical shaped pattern of etch pit scattered light, as shown in FIG. 3f. A mixed set of etch pits comprising both circular and elliptical shapes in close proximity, as shown in FIG. 3g, will produce an irregular shaped etch pit scattered light pattern, as shown in FIG. 3h.

Referring now momentarily to FIGS. 1 and 2, the bottom aperture 26 of the light integrating sphere 22 is sized and positioned to admit most of the etch pit scattered light 30, for example, about 20 to 40 degrees from normal. The top aperture 24 is preferably sized and positioned to not allow light rays 30 scattered from the surface 20 wider than about five degrees from normal to pass therethrough. In other words, the top aperture 24 preferably coincides substantially with the void center circle 73 of the etch pit scattered light pattern 72 of FIG. 3b. Consequently, most of the etch pit scattered light 30 is captured and retained by light integrating sphere 22, where it is integrated to produce intense diffuse light 32 to induce a strong signal from photodetector 40. At the same time, very little of the etch pit scattered light 30 escapes through top aperture 24 to reach the second photodetector 50, so any signal produced by photodetector 50 is not influenced significantly by etch pit scattered light 30.

Referring now primarily to FIGS. 4a and 4b, a grain boundary 90 in a polycrystalline material, when etched as described below, will produce a V-shaped groove 92 that is essentially one-dimensional and runs the length of the grain boundary 90 along the surface 20 of the sample 14. Light incident on such etch grain boundaries 90 is scattered in a substantially fan-shaped distribution 94 in a plane that is perpendicular to the surface 20. When the fan-shaped scattered light distribution 94 is projected onto a plane 96 that is parallel to surface 20, it forms a pattern, 98 of divers elongated spots 101, 102, 103, 104, 105, 106, 107, 108 . . . as illustrated in FIG. 4b. The circular center spot 100 is substantially specular reflection or retroreflection from the V-shaped groove 92 or surface 20.

Referring again to FIG. 2, a polycrystalline sample 14 is illustrated on X-Y stage 12 with a grain boundary 90 and a V-shaped etch groove 92 where the grain boundary 90 intersects the surface 20, similar to that illustrated in FIG. 4a and described above. The surface 20 also has etch pits 70 where dislocations intersect the surface 20; however, the size and density proportions are not illustrated to scale because of limitations inherent in these kinds of illustrations for microscopic features. As shown in FIG. 2, a fairly wide or large diameter beam 18 is used to illuminate a sufficiently large portion of the surface 20 to obtain a good statistical sample of etch pits. Therefore, there is no attempt to focus the beam 18 to a point on the surface 20. In fact, it is preferred that a point focus is avoided. Generally, it is preferred to include at least two hundred etch pits in the illuminated area, which usually requires a beam diameter of about 500 to 1,000 μm.

As also shown in FIG. 2 for purposes of illustrating additional features of this invention, the V-shaped grain boundary etch groove 92 is positioned in the area illuminated by beam 18. Consequently, both an etch pit scattered light pattern, such as one of the patterns illustrated in FIGS. 3a through 3h, and a grain boundary etch scattered light pattern, such as the pattern 98 illustrated in FIGS. 4a and 4b, are produced together. The result is a combination etch pit light scattered pattern, such as pattern 72 of FIGS. 3a and 3b, combined with a grain boundary etch pattern 98 of FIGS. 4a and 4b. The combination of these patterns 72 and 98 is illustrated in FIG. 5. The specular light components 38 of FIGS. 2 and 4a that produce center spot 100 of FIGS. 4b and 5, and the near specular light components 34 and 36 of FIGS. 2 and 4a that produce the inside spots 101 and 102, respectively, of FIGS. 4b and 5 deviate from specular normal for the most part less than five degrees (5°). Therefore, as best illustrated in FIGS. 2 and 5, those light components 34, 36, and 38 and their corresponding spots 100, 101, and 102 are for the most part confined in the center area 73 that is substantially devoid of etch pit scattered light 30. Therefore, as shown in FIG. 2, the top aperture 24 of the light integrating sphere 22 allows the light components 34, 36 and 38 scattered or reflected by the grain boundary etch groove 92 to pass out of the light integrating sphere 22. Therefore, the limited pattern shown in FIG. 6 comprising only spots 100, 101, and 102 reach the plane 112 of the center block aperture 44 in FIG. 2. The specular light component 38 is subsequently blocked and eliminated from the system 10 by the center block aperture 44 as mentioned above. Consequently, only the near specular light components 34 and 36 scattered by the grain boundary etch groove 92 pass through the light integrating sphere 22 and reach the second photodetector 50. Substantially all of the etch pit scattered light 30 is captured in the light integrating sphere 22, as described above, and is detected only by the first photodetector 40. As a result, the signal produced by the second photodetector 50 is essentially the result of a grain boundary 90 in the area of illumination by beam 18. This signal on lead 52, therefore, can be processed, discriminated, and used for detecting and mapping grain boundaries in polycrystalline materials as distinct from dislocation defects.

In FIG. 2 the light components 34, 36, and 38 that pass through the top aperture 24 of light integrating sphere 22 are collimated by a lens 114, reflected out of the normal path by beam splitter or partially silvered mirror 116, and directed to the center block aperture 44. As mentioned above, the projected light components 34, 36, and 38 and which form spots 100, 101, and 102 that reach plane 112 of aperture 44 are substantially as shown in FIG. 6. The aperture 44 has an annular opening 45 large enough to pass substantial portions of the near specular components 34 and 36 and a center block 46 large enough to block the specular light component 38. The convex lens 48 converges and focuses the near specular light components 34 and 36 onto the second detector 50, so that the projection of the light, essentially comprising the near specular light components 34 and 36, appears as the near spots 101 and 102, illustrated in FIG. 7, without the specular light component 38 and circular center spot 100. It is important to eliminate the specular light component 38, because a substantial portion of the specular light component 38 can be, and probably is, light reflected from smooth, nondefective areas of the surface 20 of the polycrystalline material 14 adjacent the grain boundary 90, thus could also be present in the signal from the second photodetector 50, even if there is no grain boundary in the area of illumination. Elimination of the central or specular light component 38 insures that the only signal from photodetector 50 is from a grain boundary defect.

It may be noted that the more divers components of the grain boundary scattered light 94 that produce the intermediate spots 103–108 in the pattern 98, as illustrated in FIGS. 4a, 4b, and 5, will not pass through the top aperture 24 of light integrating sphere 22, thus will be captured along with the etch pit scattered light 30 inside the light integrating sphere 22 of FIG. 2. If those intermediate components of the grain boundary scattered light 94 are intense enough, they can affect and cause erroneous signals of etch pit density (EPD) from the first photodetector 40. In fact, if the beam 18 was narrowed to a point, and if the point was focused on the grain boundary etch 92, the resulting grain boundary scattered light 94 intensity inside the light integrating sphere 22 would probably predominate and could even swamp out any etch pit scattered light intensity. Actually, the first photodetector 40 could operate as a grain boundary 90 detector in that configuration.

On the other hand, the effect of the intermediate components of grain boundary scattered light 94 can be minimized in several ways. First, the incident beam 18 can be operated with a wide diameter, thus illuminating a larger area of etch pit defects 70 on the surface 20 of the polycrystalline material 14. Such wide area illumination increases substantially the intensity of etch pit scattered light 30 inside the light integrating sphere 22 as compared to the grain boundary scattered light 94. Further, since the problem of the grain boundary scattered light 94 is essentially one dimensional, while the pattern of the etch pit scattered light 30 is two dimensional, a larger area illumination can minimize the effect of the grain boundary scattered light 94 inside the light integrating sphere 22 that is detected by the first photodetector 40. Additional electronic signal conditioning and processing, as described below, can further minimize the residual effects of the grain boundary scattered light 94 detected by first photodetector 40.

Another adjustment that can minimize the effects of divers components of grain boundary scattered light 94 is to increase the distance between the bottom aperture 26 of the light integrating sphere 22 and the surface 20 of the polycrystalline material 14. Increasing this distance can allow the furthest-out components of the grain boundary scattered light 94, which spread at a large angle to normal, i.e., a smaller angle to the surface 20, to pass beneath the light integrating sphere 22 and avoid capture by the bottom aperture 26. Of course, raising the light integrating sphere 22 to an even larger distance off the surface 20 could cause the outer fringes of the etch pit scattered light 30 to be excluded, too, which could be counterproductive. Widening the bottom aperture 26 along with increasing the distance between the light integrating sphere 22 and the surface 20 could help to capture the outer fringes of the etch pit scattered light 30, but wider apertures can also allow diffuse light inside the light integrating sphere 22 to escape, thus lowering intensity and signal strength from the first photodetector 40. Therefore, there is a balance that can be found and maintained between incident beam 18 size, distance between light integrating sphere 22 and surface 12, and sizes of apertures 24 and 26 that provides optimum results and signals for a particular system 10 used in conjunction with a particular polycrystalline material 14. A larger beam 18 size can also increase the size of the raster increments needed to scan a sample 14 as well as increasing the statistical base of the method used in this invention, which detects statistical defect densities instead of detecting and counting individual etch pits. Therefore, the larger raster increments along with the increased statistical base of defect densities that result from a larger sized beam 18, as described above, can combine to increase substantially the defect mapping speed and efficiency according to this invention.

Referring again to FIG. 1, the etch pit density (EPD) signal on lead 42 is directed to a first amplifier circuit 120, where it is conditioned, filtered, cleaned up, and amplified. Likewise, the grain boundary signal on lead 52 is directed to a second amplifier circuit 122, where it is also conditioned, filtered, cleaned up, and amplified. Both signals are then directed via leads 124, 126, respectively, to an algebraic summing circuit 128, where the etch pit or dislocation signal is algebraically summed with (subtracted from) the product of an empirically determined constant times the grain boundary signal to produce a new signal that is indicative of grain boundary for mapping purposes. Initialization can be made on a location that is known to be all dislocation defects and no grain boundary defects. In the opposite mode, the grain boundary signal can be algebraically summed with the product of a constant times the dislocation signal to produce a net signal that is indicative of dislocation density.

The dislocation density and grain boundary signals are fed into a computer 130 along with X-Y position information from the stage 12 via connection 132. The data is stored in a high-speed buffer memory. Commercially available computer software, such as "Lab View," produced by National Instruments, of 6504 Bridgepoint Parkway, Austin, Tex. 78730, and "Delta Graph," produced by Deltapoint, Inc. of 2 Harris Court, Suite B-1, Monterey, Calif. 93940, can be used, with appropriate modifications for particular system hardware and other parameters that would be within the capabilities of persons skilled in this art. Preferably, however, customized software as described in detail below can be used in the computer 130 in order to provide expanded flexibility such as calibration of the system 10. This customized software may alternatively be oriented toward commercial or research applications.

Either the commercially available software or the customized software can be employed to make a map of the dislocation densities and grain boundaries in the material 14, and detailed analysis or displays can be made on the monitor 134 and by a color printer or plotter 136. For example, a defect density map produced with the system 10 according to this invention is shown in FIG. 9. Alternatively, the grain boundary data can be used to produce a grain boundary map. For example, the grain boundaries shown in the microscopic photograph of FIG. 10a was scanned with the system 10 of this invention, and the grain boundary map in FIG. 10b was produced with the data. Alternatively, analog signals from the photodetectors 40 and 50 can be processed by the analog display controller 138 to directly display the dislocation and grain boundary distributions on a storage oscilloscope 140 or an X-Y recorder 142.

The preferred etching process for use with this invention is a variation of the chemical etching procedure published by the inventor in B. L. Sopori, "A New Etch for Polycrystalline Silicon," *J. Electrochem. Soc.:* SOLID-STATE SCIENCE AND TECHNOLOGY, Vol. 131, No. 3, Page 667 (1984), which produces substantially equal volume etch pits, regardless of dislocation orientation, which is incorporated herein by reference. The following mixtures are used in defect etching:

1) 1:1 of hydrofluoric acid (HF) to water, referred to as the HF rinse.
2) 1:1 of nitric acid ($HNO_3$) to water, referred to as the $HNO_3$ rinse.
3) 36:15:2 of hydrofluoric acid to acetic acid ($CH_3COOH$) to nitric acid, referred to as Sopori etch.
4) 2:1 of sulfuric acid ($H_2SO_4$) to hydrogen peroxide ($H_2O_2$), referred to as Piranha.

The steps of this procedure include:

a) Make sure the sample to be etched is clean by checking it under the microscope. If the sample is not clean (there are blobs visible on the surface), it should be cleaned.

b) Heat the Piranha on a hot plate (not shown) to 80° C. (a setting of "LOW"). It should take approximately 15–20 minutes to heat the Piranha. It is hot enough when it begins to gently bubble. Do not let the Piranha reach a full boil. If the Piranha was just mixed it does not need to be heated; the heat generated in mixing the $H_2SO_4$ and $H_2O_2$ is adequate.

c) Place the sample in a Teflon sample holder and then let the sample sit in the Piranha for 15 to 30 minutes. The Piranha cleans off any remaining small bits of wax or dirt on the surface of the sample. After the sample has soaked, rinse it off with a stream of deionized (DI) water and blow it dry with an air gun (not shown).

d) The HF rinse, the $HNO_3$ rinse, and the etch should be poured into separate, labeled, plastic one-liter beakers. Fill a two-liter beaker with DI water for rinsing the samples after etching.

e) Dip the sample into the etch and gently wave it back and forth for approximately 30 seconds after bubbles begin to form. Remove the sample from the etch and immediately dip it into the beaker of DI water. Gently wave the sample back and forth for several seconds and then risen it with a stream of DI water. Dry the sample with the air gun.

f) Dip the sample in the $HNO_3$ rinse and gently wave it back and forth for approximately 15 seconds. Remove the sample and dip it into the beaker of DI water for several seconds. Rinse the sample in a stream of DI water and then dry it with the air gun.

g) Dip the sample in the HF rinse and wave it back and forth for approximately 15 seconds. Remove the sample and dip it into the beaker of DI water for several seconds. Rinse the sample in a stream of DI water and then dry it with the air gun.

A second embodiment system 200 is shown in FIG. 11. In this embodiment, the light integrating sphere 22 is positioned far enough away from the surface 20 to accommodate the collimating lens 114 and beam splitter 116 between the light integrating sphere 22 and surface 20. The beam splitter 116 diverts part of the grain boundary scattered light 96 and etch pit scattered light 30 toward the second photodetector 50 before reaching the light integrating sphere 22. In this embodiment, the blocking aperture 244 passes only the outer portions 210 and 212 of the grain boundary scattered light 96 to the second detector 50 and blocks everything else. The bottom aperture 26 of light integrating sphere 22 is large enough to admit the etch pit scattered light 30, but small enough to block the outer portions of grain boundary scattered light 96 that passes through beam splitter 116. The near specular portions 34 and 36 of grain boundary scattered light 96 that pass through the beam splitter 116 also pass out the aperture 24 of light integrating sphere 22. Therefore, it is only the intermediate portions of grain boundary scattered light that enter and are captured in the light integrating sphere 22 along with the etch pit scattered light 30. These intermediate portions of grain boundary scattered light, as in the embodiment 10 described above, are not sufficient to swamp or degrade the intensity signal for etch pit scattered light 30 as long as the incident beam 18 illuminates a wide enough area on surface 20.

A third embodiment system 300 is shown in FIG. 12. The system 300 is similar to the system 10 shown in FIG. 1 with like components referenced with a prime designation. A first laser 16' provides a beam 18' of light at a relatively long wavelength, preferably greater than 8000 Å, for example approximately 9000 Å. A second laser 302 provides a beam 306 of light at a wavelength different from the first laser 16', preferably less than 7000 Å, for example 6328 Å. A lens 304 establishes the width of the beam 306 from the second laser 302. A lens 308 establishes the width of the beam 18' from the first laser 16'. A beam splitter 310 is placed between the light integrating sphere 22' and the first laser 16' in such a position as to allow the beam 306 from the second laser to be positioned substantially parallel with the beam 18' from the first laser 16' and directed toward the crystalline material or sample 14'. The beam splitter 310 has a central portion 311 which is reflective while the remaining portion is not. Consequently, the specular portion of the light reflected from the surface 20' of the material 14' is reflected back toward the second laser 302 while the near specular light components 34' and 36' pass by the beam splitter 310 and are directed to the second photodetector 50'.

A signal 312 is provided from the first laser 16' to the computer 130' containing information related to the total transmitted power in the beam 18'. Similarly, the second laser 302 provides a signal 314 to the computer 130' containing information related to the total transmitted power in the beam 306.

A third photodetector 316 is positioned in the opposite side of the light integrating sphere 22' from the first photodetector 40'. A first filter 318 is positioned in front of the first photodetector 40' to allow reflected light from laser beam 18' to pass therethrough but with transmission characteristics which cause reflected light from laser beam 306 not to pass therethrough. Similarly, a second filter 320 is positioned in front of the third photodetector 316 and allows reflected light from laser beam 306 to pass therethrough while blocking reflected light from laser beam 18'. The third photodetector 316 produces a signal 322 indicative of the intensity of the diffused light 32' which is of the wavelength of laser beam 306. This signal 322 is transmitted to the signal processing and control unit 60' where a third amplifier circuit 324 conditions, filters, cleans-up and amplifies the signal 322 before supplying a third amplified signal 326 to the analog display controller 138' and the computer 130'.

The lens 304 is chosen so that the beam 306 is preferably of a width similar to the width of a grain boundary etch, or 0.1 mm. This relatively small beam width produces a sharper grain boundary definition since the sharpness of the grain boundary image is determined by the convolution of the grain boundary groove size and the beam width. The lens 308 is chosen so that the beam 18' is preferably in the range of 0.5–1.0 mm to provide a sufficient statistical sample of dislocation defects. In this way, this embodiment can be optimized separately for each of the type of defects rather than selecting a compromise beam width.

The use of two light beams, each having a different wavelength, provides another advantage. Namely, variations in the size of the etch pits can be corrected for by the use of the dual wavelength system. The variations can occur from variations in the time duration of the etching process or the exact composition and cleanliness of the etchant solution. FIG. 13 shows graphs of the normalized signal received from the diffuse light reflected off the material 14' as a function of etch pit density. It can be seen that this function is also dependent on the etch pit size and the wavelength of the light. Curve 400 shows the relationship between the etch pit density and the normalized signal, with a first etch pit size and a relatively long wavelength. Curve 402 shows the relationship, with the first etch pit size and a relatively shorter wavelength. At a particular etch pit density 403, a difference 404 or a ratio can be calculated between the curve 400 and the curve 402.

Curve 406 shows the relationship between the etch pit density and the normalized signal, with a second etch pit size (which is larger than the first) and the relatively long wavelength. Curve 408 shows the relationship, with the second etch pit size and the relatively shorter wavelength. At the same particular etch pit density 403, a difference 410 or a ratio can be calculated between the curve 406 and the curve 408. It can be seen that the difference 410 is smaller than the difference 404. This relationship between the differences 404 and 410 can be exploited to determine and correct for variations in etch pit size.

It is also possible to obtain maps of reflectance and photoresponse for a photovoltaic device or solar cell (also referenced as 14') which has been produced from crystalline material 14'. With the system 300 (FIG. 12) the signals from the photodetectors are summed to obtain total reflectance. By translating the X-Y table 12', a reflectance map can be produced. Maps of diffuse, specular, and total reflectance can be produced for each wavelength produced by the lasers 16' and 302. To perform light beam induced current (LBIC) measurements on the photovoltaic device 14' the light integrating sphere 22' is mounted in such a manner as to allow it to be moved laterally away from the X-Y translation stage or table 12'. A pair of electrical leads 328 and 330 are attachable to opposite sides of the photovoltaic device 14'. The leads 328 and 330 are also connected to the respective input terminals of a low-input-impedance amplifier 332 which supplies a signal 334 to the analog display controller 138' and the computer 130' indicative of the current flowing through the leads 328 and 330 and the photovoltaic device 14'.

The reflected power is subtracted from the total transmitted power as communicated by the signal 312 to the computer 130'. From this difference, the total absorbed power (by the photovoltaic device 14') can be calculated. The current induced through the device 14' by the incoming light is measured by the amplifier 332 and an optical energy-to-electrical energy conversion efficiency (photoresponse) can be calculated. These calculations can be repeated as the material 14' is rastered by the X-Y table 12' so as to create a two-dimensional "map" of photoresponse. External photoresponse is a measure of the electrical power produced as a function of the total transmitted optical power. Internal photoresponse is a measure of the electrical power produced as a function of the total absorbed optical power.

Dual wavelengths provide several advantages to the LBIC measurements. The longer wavelength light tends to penetrate deeper into the material 14' than the shorter wavelength light, and thus the longer wavelength light can be used to provide information about the property of the material such as the minority carrier diffusion length. This parameter is the length an electron (which is the minority carrier in P-type material) can go toward the N-P junction without combining with a hole. On the other hand, the shorter wavelength light provides information relating to the near-surface features of the material 14'. These features may include grain boundaries and N-P junction characteristics. It is important to examine the non-uniformities in the material or photovoltaic device because the inefficient portions of the material are a sink to the power generated by the more efficient portions of the material. The non-uniformities may be due to the growing process, other defects, the junctions or the anti-reflective coating on the material.

Among the many possible alternatives which could be used in the above-described embodiments are the substitution of a non-laser light source for the laser. The light source need not be coherent. However, with the third embodiment it is desirable for the light source to have a relatively narrow color output. In addition, it would be possible to use mirrors or a separate light source to provide the beam for LBIC to a remote section of the material 14' as an alternative to moving the light integrating sphere 22'.

The customized software which may be used by the computer 130 generally includes the following functional features: (1) determine or define the dimensions of the area to be scanned and the step size in translating the X-Y table 12 (which is driven by a stepper motor which is not shown); (2) acquire data; (3) display data; and (4) calibrate the system 10. Included within the second, third, and fourth generalized functions are the equations employed to calculate the various parameters such as reflectance, conversion efficiency (in LBIC mode), dislocation defects and grain boundary magnitude.

The determination/definition function is performed as shown in FIG. 14. First, the operator positions the X-Y table 10 using manual motion control buttons to the upper left-hand corner of the scan area and signals through keyboard entry to computer 130 when accomplished (420). Specifically, the scan area is defined by first locating the zero reference point, arbitrarily chosen as being the upper left corner of the area to be scanned. The motion of the X-Y table is manually controlled by clicking the mouse on arrow keys that indicate direction. As the table moves, the X and Y coordinates are displayed in the boxes showing the home position. When the table is properly positioned, the "YES" box is clicked, responding to the prompt to move to the upper left corner. The X and Y coordinates change to zero, indicating that the current point is now recognized as "home", or the zero reference. Second, the X and Y position of the upper left-hand corner of the scan area is stored in memory (422).

Third, the operator positions the X-Y table 10 using manual motion control buttons to the lower right-hand corner of the scan area and signals through keyboard entry to computer 130 when accomplished (424). Specifically, after the table is moved the "YES" box is again clicked, in response to the prompt to move to the bottom right corner. The X and Y coordinate boxes show the coordinate values chosen. Fourth, the X and Y position of the lower right-hand corner of the scan area is stored in memory (426). The system will assume that these two positions completely define the scan area, since a rectangular scan area is assumed.

Next, the operator is prompted to enter a value for the step size between 0.001 and 0.010 inches (430). The default step size is 0.005 inches, and if that is the desired value the scan can be started immediately. Otherwise, the menu item "Select step size" must be chosen, and a value entered. On SMDS-2, step size is limited by the time to complete a scan and the resolution of the stepper motors. The motor limitation is 0.001 inches. To scan a large area at this small step size would result in excessively long scan times. An arbitrary upper time limit of 1.25 to 1.5 hours to complete a scan was chosen. In order to meet this time limitation, larger step sizes must be chosen for the larger scan areas. The table below lists the maximum square edge dimension that can be scanned within this time. As a practical matter, the maximum sample size is assumed to be 4 inches. The table motion limitation is 5 inches square.

| Inches per side | Min. step size |
| --- | --- |
| 2.0 | .001 |
| 2.7 | .002 |
| 3.3 | .003 |
| 3.8 | .004 |
| 4.2 | .005 |

As a note, a 4 inch square sample scanned at 0.005 inch steps generates a 2.4 MB disk file. Lastly, the step size is stored in memory (432).

The second function includes scanning the defined area to acquire the data as shown in FIG. 15. First, the scan information is initialized and a data file is opened (440). Specifically, this includes: set the motor speed and acceleration constants; calculate the size of the 2 screen images, and locate them as non-overlapping windows; determine the number of motor steps between sample points and set up counter; set up the scan sequence to perform at each sample point; set up the scan sequence for one row of data; generate table motion program and send it to the table controller; open a disk file to store the acquired data; and write the disk file header, including all of the scan parameters.

Next, the X-Y table is set up for scanning a row of the area (442). This is accomplished with the help of a National Instrument control program for the data acquisition board. This extension to the Visual Basic language allows data to be captured to a memory array based on the pre-defined point and row parameters.

Then, the X-Y table 12 is moved across the row, acquiring data while scanning and storing data in RAM (444). Send the table controller the command to execute the previously defined motion for one row. This involves traversing the width of a scan row, bringing data at each sample point into an array in RAM memory. The table then moves down one row width.

Next, at the completion of a row, the data is stored to a hard disk (not shown), while performing the calculations for each data point and displaying a color for that data point (446). Reading one sample consists of a data value for the Defect Map and Grain Boundary Map from the RAM array. This data is then processed as follows. The data values for the Defect Map and Grain Boundary Map are stored as two 16 bit integers. Color calculations are based on several optional color processes. The process selected previously by the user will be the process used to do the color calculation.

Each image is allocated an area on the screen proportional to the physical dimensions of the silicon scan area within the limits of the computer screen size. If more data samples are stored in this image area than the area allows, the windows environment compresses the data by overwriting pixels. The pixel visible will be the last pixel written to that location in the image. After that, a test is made to see if the last row has been processed (448). If not, then the flow returns to the set-up step (442).

If the last row has been processed, then the minimum and maximum value for each data parameter are stored in the data file with a date stamp and the file is closed (450). As the scan is taking place, the samples are examined to determine the maximum and minimum signal levels for each image. When the scan is complete, these values are written to the disk file header. Later, when the data is displayed, this information can be used to distribute the spectrum of available screen colors evenly between the maximum and minimum signal values. This results in a maximum resolution display of signal variation. Each image stored in the disk file has an allocated comment area in the header file. As the disk file is closed, the current date and time is stored in this comment area so that subsequent display of the date can be identified. This comment area can be changed at will to include word explanations of the scan information. The last act of the scan function is to close the disk file, terminating the acquisition action. The file can now be used to display the data in any one of several color formats.

The third function includes displaying the acquired data as shown in FIG. 16. First, the operator selects the file to be displayed (460). Using the screen icons, the disk, directory and file can be selected. The default file location is c:\vb\data. Second, the operator is provided the opportunity to add or modify comments in the file (462). The default comment for an image is the date stamp indicating the date and time the scan was complete. The maximum length of the comment field is 30 characters. The user can add to or change the comment field at any time. It will be permanently added to the disk file when the "Save Comment" button is clicked. Each image within the file has an independent comment field.

Third, the operator selects the color format (464). There are three color formats. The first is a fixed format, which can be calibrated to certain dislocation densities or grain boundary signal levels. The second format distributes 16 colors evenly between the maximum and minimum signal levels for the image. This format is the best for showing details of signal variation. The third format bases the displayed image on the signal of the primary image minus the companion image attenuated by a user selectable scaling factor.

Fourth, the operator selects the display type (466). Display types can either be a dual display of both images, or a single display of the dislocation map or grain boundary map. Because of monitor display constraints, the normal VGA screen resolution may not display images at full resolution. For scan areas less than 1.2 inches, both images can be displayed at the same time at full resolution. For scan areas up to 2.4 inches, single images can be displayed at full resolution. For images larger than about 2.4 inches, the normal VGA screen will display the images at reduced resolution. However, one can go into high resolution mode of the monitor (1280×1024) to display and print a 4 by 4 inch scan area with 0.005 inch step size at full resolution. Screen resolution is set in the Windows environment by selecting [Main—Setup—Options—Change System Settings—Display] from the program manager window. After changing screen resolutions, the Widows program has to be restarted. Fifth, the data is displayed in the selected format and type (468).

Sixth, the operator is provided the opportunity to send the displayed data to a printer (470). What is seen on the screen is what is sent to the printer. Any scan area can be displayed on the screen at full resolution. When this is done the printer will also print at full resolution. Next (472), if the operator wishes to create more displays the flow returns to one of the previous steps (460), (464), or (466) depending on whether the operator wishes to display a different file, display the current file in a different format, or display the current file in a different display type, respectively. If no more displays are desired, the flow exits (474) this function. It is possible to return to the main menu to continue scanning or to exit to the window environment and terminate the program. Each image stored in the disk file has an allocated comment area in the header file. As the disk file is closed, the current date and time is stored in this comment area so that subsequent display of the data can be identified. This comment area can be changed at will to include word explanations of the scan information. The last act of the scan function is to close the disk file, terminating the acquisition action. The file can now be used to display the data in any one of several color formats.

The fourth function includes calibrating the system with the use of standard samples having a known quantity of the parameter to be calibrated, such as specular reflectance, diffuse reflectance, dislocation density, LBIC, etc. These standard samples have a predetermined quantity of the desired parameter so that a measurement of the amount of that parameter can be made by the system 300 on the standard sample and compared to the known amount of that parameter. A calibration constant equal to the ratio of the known amount to the measured amount can be created. This calibration constant can then be used in all subsequent calculations by multiplying the constant times the measured amount to obtain the compensated, measured amount of that parameter.

A fourth embodiment system 400 is described below. Generally, the fourth embodiment is a more refined and detailed version of the third embodiment known as the Semiconductor Device and Material Characterization System (SDMCS). Some portions of the following description are repetitive of the description of the first three embodiments. SDMCS is a high-speed laser scanning system that produces maps of the spatial distributions of crystal defects such as grain boundaries (GB) and dislocations in semiconductor wafers (dislocation density or DD), reflectance of solid substrates, and photoresponse of photovoltaic devices. In contrast with most scanning systems that use scanning beams, this system employs a scanning substrate with fixed beams. This approach of scanning prevents errors due to beam distortions, and changes in the reflectance and absorption in the material/device due to oblique incidence of the beam on the test devices. Consequently, SDMCS can easily provide quantitative information of the material/device parameters such as dislocation density, diffuse reflectance, specular reflectance, true internal response of the photovoltaic devices in mA/mW, and the minority carrier diffusion length. In addition to performing semiconductor characterization, this system has other applications in evaluating morphology of surfaces for control of polishing and optical properties, and in process control of many other materials. The system was originally designed to rapidly analyze large-area silicon wafers and devices. However, these applications can be extended to other semiconductors such as GaAs and Ge.

The SDMCS includes software written to provide the operator an extensive capability to acquire and display various parameters in a quantitative manner. The software keeps track of all the calibration constants and produces displays of parameters in a very convenient format. Furthermore, the system has the capability for correction of etch pit size when used to produce defect maps. This capability compensates for errors that may arise from variations in the defect etching process.

In order to produce quantitative data, the system requires calibration of detectors. Although, once calibration is performed, the system can be used for a long period of time without recalibration, it is recommended that calibration samples be run through the system frequently.

SDMCS has the following modes of operation:
Defect (dislocation and grain boundary)
Reflectance (diffuse, specular, and total)
External LBIC
Internal LBIC (minority carrier lifetime/near surface recombination)
Calibration The following calibration standard samples are supplied:

Specular reflectance standard sample. A polished silicon wafer is used. Polished silicon has a specular reflectance of 36% at 630 nanometers and 30% at 905 nanometers. This is discussed further in *Solar Cells*, Volume 8, at page 249 (1983) by B. L. Sopori and R. Pryor which is hereby incorporated by reference.

Diffuse reflectance standard sample. These are available from Labsphere, Inc. of North Sutton, N.H.

Calibrated solar cell standard sample. A cell having a known spectral response is used. Such cells can be obtained from the assignee or elsewhere by measuring the performance of the solar cell. This is done by illuminating the cell with narrow-band, filtered light of known power and measuring the short circuit current. The spectral response at this band of wavelength is:

$$SR = J_{sc}/P_{il}$$

where SR is the spectral response;
$J_{sc}$ is the short-circuit current due to illumination;
$P_{il}$ is the incident light power; and
SR has units of milliamps per milliwatt (mA/mW).

This procedure is described as a part of cell testing procedures, for example in *Solar Cells*, Volume 24, at page 371 (1988) by K. Emery, et al., which is hereby incorporated by reference.

Dislocation density standard sample. A sample with a standard or known amount of dislocation defects is generated by heating the sample (a silicon wafer) in a non-uniform manner. The amount of defects is obtained by standard techniques such as counting etch pits under an optical microscope. Alternatively, these samples can be obtained directly from the assignee.

PRINCIPLES OF OPERATION

The principles of SDMCS for various modes of operation are briefly described below.

Defect mapping:

The SDMCS is a unique instrument that uses simple optics to distinguish and count different defects by analyzing the light scattered by them. The defect identification is done by separating the light scattered by various defects, while a statistical method is used to rapidly count defects. These approaches of defect identification and counting differ from conventional methods that are based on the computer analysis of defect images. Because of the optical recognition (as compared to the recognition based on image analysis by computer software), the system is extremely high speed, simple to use, low-cost, and does not require highly skilled engineering personnel to operate. The defect mapping of a silicon wafer involves the following two steps.

The sample to be scanned first undergoes a unique defect etch known as the "Sopori etch," described above in conjunction with the first embodiment. This etch delineates dislocations on all crystal orientations, producing etch pits of the same optical scattering cross-section and V-shaped grooves at the grain boundaries (GBs). When such a defect-etched sample is illuminated by a beam of light, dislocations and grain boundaries scatter light with different divergence angles, and the light from regions of zero defects is specularly reflected.

The etched sample is then scanned under a laser beam. The scattered light with different divergences are separated and measured by different detectors. The light scattered by dislocations is collected by an integrating sphere and measured by a optical detector to produce a statistical count of the local dislocation density. The total integrated scattered light is proportional to the number of dislocation etch pits illuminated by the beam. In this manner, a statistical count of dislocations is made. The reflected light scattered by the grain boundaries emerges out of the integrating sphere and is measured by a separate optical detector. The signals from the two detectors are digitized and fed into a computer along with the position signals from the X-Y scanning stage. The data is stored in a high speed buffer memory and is then used to make maps of dislocation and/or grain boundary distributions in the sample.

Defect mapping also uses a method to correct for any variations in the etch pit size. Typically, the etch pit size can be maintained constant by controlling the composition of the defect etch and the etching time. However, variations may arise because of the differences in the manual etching procedure as performed by various people. An increase in the etch pit size will erroneously indicate a higher dislocation density. To correct for any variations in the etch pit size, the SDMCS exploits wavelength dependence of the scattering from etch pits. It is determined that increase in the scattering due to an increase in the etch pit size is smaller for a longer wavelength light compared to that at a shorter wavelength. This comparison is used to determine a size-factor to correct for change in the etch pit size.

Reflectance

SDMCS can simultaneously map the specular and diffuse components of the reflectance of a test sample. It also offers capability to combine diffuse and specular reflectance to map the total reflectance. The system has the capability to produce such maps at two wavelengths, $\lambda_1=0.63$ μm and $\lambda_2=0.905$ μm. In the reflectance measurement the sample is illuminated with the selected laser at a normal incidence. The light scattered within a solid angle of 5° is collected by a lens and measured to determine the specular reflectance. The light scattered within solid angles >5° is collected by an integrating sphere and measured to determine diffuse reflectance. These components of the reflected light can be combined to map the total reflectance of the sample. Standard samples are provided to calibrate both specular and diffuse reflectance. Note: the angular ranges that define the specular and diffuse components can be adjusted by suitably changing the entrance and exit apertures of the integrating sphere.

External LBIC

Light beam induced current mapping capability is offered at two optical wavelengths of excitation, $\lambda_1=0.63$ μm and $\lambda_2=0.905$ μm. Because the absorption depth at these wavelengths is very different, they offer a capability to separate the near-junction and the bulk responses. For example, in silicon devices the absorption depth at $\lambda_1=0.63$ μm is only about 2 μm; the response represents mainly the contributions to the photocurrent from the near-surface region such as the junction. When mapping with the excitation wavelength of $\lambda_2$ (equal to 0.905 μm), one can obtain the response from deep within the device. As discussed below, the response at this wavelength can be used for mapping of minority carrier diffusion length.

Internal LBIC

The capability of mapping both the reflectance and the external LBIC response can be combined to develop maps of the internal photoresponse. The internal photoresponse maps are free from variations in the reflectance that accompany local changes in the surface morphologies such as surface texturing (particularly prominent in multi-crystalline solar cells), and non-uniformities in the antireflection coatings.

Of particular interest is the internal photoresponse of a photovoltaic device taken with long wavelength excitation. This response is proportional to the minority carrier diffusion length (L). To determine L, the system makes measurements of external LBIC using Laser2 ($\lambda_2=0.905$ μm), and separates the effect of reflectance using the following relation $$LBIC_{int}=LBIC_{ext}/(1-R_{tot})$$

The effective diffusion length, $L_{eff}$ is proportional to $LBIC_{int}$. Thus, $$L_{eff}=constant \times LBIC_{int}$$

The constant in the above equation is related to the collection efficiency of the generated carriers, and hence, is related to the junction properties of the device. The $L_{eff}$ maps for any device can be generated by calibrating the system with a reference cell of the same junction characteristics as the test cell.

System configurations

FIG. 17 is a schematic showing various components of SDMCS. The light beams from Laser1 and Laser2 are shaped by the corresponding apertures and the lenses. A part of the light from each of the lasers is separated by means of the beam splitters BS1 and BS2 to monitor the laser power by detectors LPD1 and LPD2, respectively. Each light beam goes through the integrating sphere (IS) and illuminates the sample at normal incidence. The integrating sphere captures the light scattered by the dislocations in the test sample (TS). The scattered light corresponding to the illumination by Laser1 and Laser2, is measured by detectors DD1 and DD2, respectively. Filters $T\lambda_1$ and $T\lambda_2$ are used to ensure that the detectors DD1 and DD2 receive only the light from the corresponding laser. The specular and the near-specular light emerging from the integrating sphere is directed to the grain boundary detector, GBD, by the beam splitter BS1. An annular aperture, AA, is used to block the specular beam and allow only the grain boundary signal to reach GBD. In the specular reflectance mode, the AA is removed from the optical path allowing the specular (and the near-specular) beam to reach the GBD. The integrating sphere can be swung out of the path of the incident light for LBIC measurements. Each of the detectors in the system has an amplifier whose gain can be adjusted, and the amplified signals are then fed into individual channels in the computer.

In FIG. 17, each of the laser power detectors (LPD1 and LPD2) is calibrated to monitor the laser power at the sample. An alternate approach for monitoring the power from each laser can be used as illustrated in FIG. 18. In the configuration of FIG. 18, the power measurement is made directly at the sample plane by a detector which may be the standard cell used for the minority carrier diffusion length calibration.

Each configuration has its advantages. The system in FIG. 17 is more oriented for use in a production facility. However, it involves a careful alignment that may only be done at the factory or by a factory service representative. It also has two other advantages: (i) the laser power does not have to be checked independently as in the system of FIG. 18; and (ii) the laser power measurement can be utilized as a check on the system alignment, so that when the laser power, measured by the detectors LPD1 or LPD2, is less than 90% of the expected power, the computer will raise a flag indicating a possible alignment problem. Configuration 2 is simpler, uses less number of fixed detectors and channels, and directly measures power in the test plane. In this configuration, the power measurement is a part of calibration procedure.

The operations of the two systems are alike. However, in the system of FIG. 18, the signals for power measurement come from the standard cell instead of the LPD1 and LPD2. Since this substitution is quite simple, we will only discuss the system of FIG. 17.

The major elements of the system are described below.

X-Y stage:

The 5-inch X 5-inch travel X-Y stage is a Velmex MAXY4009WI-S4 system driven by Bodine 2431 motors. This stage has a resolution of 1 mil and a maximum speed of 1 inch per second. This low resolution system matches the beam size requirements for dislocation counting. The maximum speed is compatible with the data acquisition rate of the A/D board in the computer. The X-Y stage is controlled by an IBM computer that interfaces with the X-Y stage driver/controller, Velmex NF90-2, via a serial interface port.

The Velmex controller produces an electronic pulse for every step of x-motor. This pulse is used to determine table position and for sampling signals from various detectors in the system. The objective of this approach (compared to a free-running sampling clock) is to prevent distortions arising from acceleration and deceleration of the motor. Thus, the computer's knowledge of the table position (and of the location on the piece of material where a particular piece of data was obtained) is based upon the number of revolutions of the stepper motor rather than the speed of the motor which would be used if the data was tagged with or related to time rather than the stepper motor position.

Computer/Display:

An IBM PC, Dell Dimension 486/50, 430 MB HD, with an additional 8 MB RAM memory, was chosen for this system. The choice of an IBM system was made for two reasons—one, it is a lower cost system for a comparable performance, and secondly, many people in the industry still have a preference for an IBM system. The computer has a high-speed, 12 bit A/D board with three timers (National Instruments AT-MIO-16DH). A color printer, Hewlett Packard 1200C, has been included in the system for making hard copies of the maps. FIGS. 14–16 show the flow charts for various operations of the SDMCS.

Optical components:

A HeNe laser ($\lambda$=6328 Å) with a power output of 4 mW is used for short wavelength excitation. High performance detectors are installed which have a large linearity range. The integrating sphere is fabricated by Labsphere and is designed to include two detectors—DD1 and DD2. This design simplifies the alignment process. A GaAs diode laser from Melles Griot, model #51837, operating at a wavelength of 0.905 µm is used as the source for long wavelength excitation. The laser has a circular, non-polarized beam.

System Operation:

The SDMCS system is turned on by switching on the computer, the monitor, and the printer. After the system is turned on, the computer boots up the appropriate software and brings up the Program Manager which is displayed on the monitor (see FIG. 19). The Program Manager may include a variety of files that may have been saved by various users of the same computer. Identify the NREL Program box that contains Semiconductor Dev/Mat Characterization System, and click on the icon. The computer will bring up the screen image as shown in FIG. 19. This screen identifies various modes of operation and the commands that the system requires to execute different operations.

The system operation begins by the operator selecting one of the following modes:

1. DD/GB Map (Laser1 or Laser2 or both)
2. Reflectance (Laser1 or Laser2)
3. External LBIC (Laser1 or Laser2)
4. Internal LBIC (Laser1 or Laser2)
5. Calibration functions, Laser1; Calibration functions, Laser2

System Commands

Each of the modes described above includes system commands that guide the operator through a step-by-step process of acquiring the data and displaying a quantitative image of the material/device parameter. These are briefly described below.

1. Scan Area Definition

The scan area is determined by selecting the top left and the bottom right corners of the device or wafer to be scanned. In this command the visible optical beam from the Laser1 can be used as a marker. FIG. 20 is a screen image that appears when the Scan Area Definition is executed. The display shows the x and y locations of the optical beam, referenced with respect to the initial position of the beam on the sample; this initial position is identified by executing "Is the X-Y Table now at the upper left corner." The relative locations are referenced with respect to this position. The screen also computes the actual width and the length of the scan and displays them in the units of mils or microns as selected in the other commands (see Step Size). In this mode one can select a "fast" or a "slow" speed of table motion. These correspond to linear scan speeds of 1 in/min and 0.25 in/min, respectively.

Typically, a wafer or the device is over-scanned to ensure that the entire device is covered in the map. Sections of the device may be selected using this procedure. If the device is not rectangular in shape, the scan dimensions can be adjusted to cover the longest x and y dimensions of the device. Once the scan area is defined, the operator has to go back to the main menu for selection of the next operation.

2. Parameter selection

In order to properly analyze a device/substrate, the desired device/substrate parameter must be acquired and displayed such that it has sufficient spatial resolution, appropriate range of values must be adjusted to emphasize the nature of variations, and the color must be selected to produce a maximum contrast of the over-all image. This requires a proper selection of the mapping parameters. Often the values of the parameters are not known or cannot be guessed ahead of time. In such situations it is helpful to start with pre-optimized values based on the previous statistical results.

This command allows selection of parameters used in the sample scanning and the display of the images, as shown in the displayed image of FIG. 21. These parameters include: step size, the choice of color sequence for the range of parameter values (referred to as a color vector), and the ranges of parameter values that represent each color. The entire selected range of each parameter can be displayed in up to 16 colors. Eight of these 16 colors are solid colors, while the rest are different shades formed by superposition of a dark grid on solid colors. These colors are pre-set in the Standard Color List (SCL). These colors have been selected after considering the appearance of the shaded colors, the resolution requirements of the images, and the capabilities of the printer. It may be noted that although the colors in the SCL can be changed, such a change may not produce any better results. For example, brighter shades produced by superposition of a large-pitch grid may actually interfere with the resolution produced by the pixel size.

STEP SIZE

The step size is the distance between the measurements during the scan, and determines the spatial resolution of the image and the time required to complete the scan. SDMCS offers control of the step size in mils or microns. The selection of the step size is also related the monitor/printer resolution and must be appropriately selected for optimum image display. In an optimum situation, the number of steps in x and y directions required for a complete scan should equal the number of pixels on the display device, i.e. the monitor screen or the printer. This produces the display of each data point by one pixel on the display device. If the number of data points acquired exceeds the number of pixels in the assigned image size, the software will skip a suitable number of points to accommodate the image in the assigned dimensions on the display device. However, if the number of data points in the scan is less than the pixels in the assigned display size, only one pixel per data point will be displayed, thus reducing the image size.

These features can be better understood with an example. Consider a single 4-in by 4-in wafer scanned with a 10 mil step size. This scan produces 400 data points in each scan line with a total image of 160,000 pixels. The present monitor (VGA) has 640×480 resolution which is good for scanning one image of a 4-in×4-in wafer at 10 mil steps. When running a scan to display two images of a 4-in×4-in wafer (such as dislocation and GB images) the resolution on the monitor is significantly curtailed. However, the printer can print with the resolution corresponding to a 5 mil step for this size wafer. In the present system, the total scan dimensions are limited by the resolution of the printer (300 dpi). The standard printer will accommodate a 4-in×4-in wafer to be scanned with a step size of 3 mils or larger.

Color vector

Color vector allows the operator to assign up to 16 colors to represent the range of the amplitude of the parameter whose image is to be displayed. The color vector consists of two columns of color schemes—the Standard Color List (SCL) and the Display Color Sequence (DCS). The SCL is a sequence of pre-selected colors from which a new DCS can be built. The system uses only the DCS for image display. The DCS is used in conjunction with the Color Threshold values to optimize the image contrast as seen in FIG. 22. Any color in the DCS can be changed by substituting this color by another color from SCL in a two-step action—first, identify the color block on the SCL that one wishes to change to by clicking on it. This process changes the color of the middle block (see figure below) to the selected color. Next, click on the color in the SCL that is needed to replace the selected color in the DCS. Thus, the combination of DCS and Color Threshold allows the operator to adjust the number as well as the sequence of colors, and assign a range of amplitudes to these colors.

The same capability of changing the colors exists in all the display modes. This capability is very useful to produce a visual high contrast color image to discriminate between small changes in the adjacent regions of the image. For example, a light green color adjacent to a yellow color may not show up well; a change of light green to a brighter color could enhance the discrimination.

The selected information on the color vector can be saved for each of the modes by clicking on the box underneath "Save this new selection." A color vector is made part of an image file and is saved in the same file.

Color Threshold

Color Threshold allows selection of two important image parameters—first, the range of the parameter amplitude to be displayed, and secondly, the range of parameter to be displayed by each color. The number value in each of the 16 compartments of the Color Threshold vector represents the lower value of the amplitude to be represented by the color that appears in the corresponding box in the DCS. Thus, the value in a compartment number n, and the value in the compartment (n+1) define the range of color corresponding to the compartment n in the DCS, as seen in FIG. 23.

Color Threshold and the DCS allow the operator to adjust the image contrast for optimum display. The color Threshold and DCS information is converted into parameter values and displayed as color legend in the image display. The selected information on the color threshold can be saved for each of the modes by clicking on the box underneath the Color Threshold columns.

The Color Threshold command also produces a display (FIG. 23) of some valuable information about the system. It shows the calibration constants corresponding to the power from each laser. FIG. 23 below shows the display of the previous calibration constant and the present calibration constants for each laser. The display corresponds to a situation with both lasers turned off. The present displayed values are the values currently measured by the LPD1 or LPD2. The "value saved" and the "value now" inform the operator of a possible need for alignment or of a system malfunction.

3. Scan Procedure

This display, shown in FIG. 24, offers choice of laser (or lasers) that the operator wishes to use and whether a y-modulated image is desired to help the operator in deciding image display parameters. In all modes except the DD/GB, one can select only one laser at a time. Thus, if LBIC images corresponding to both lasers are desired, they can be obtained by going into the Scan Procedure, selecting each laser, and completing the scan once for each laser. However, in the case of GB/DD mapping one can select Laser1, or Laser2, or both; the last selection allows control of the beam size of each laser to optimize GB and DD definition. In addition, this mode also allows correction of the etch pit size.

Y-modulation option

The Display command includes a capability for display of the Y-modulated signal. The operator can make a line scan at one selected width of the sample or at several places. During this display the offset of the preamplifier can be adjusted to allow the signal variation to have the maximum dynamic range. The offset can be digitally adjusted in the signal channel. This offset (in terms of mA/mW) is included in the color vector. A y-modulation option is provided to:

1—offer ease in maximizing certain signals during alignment processes

2—select offset values for optimum display of colors

3—provide, in some cases, an easy-to-read amplitude display by line scans

After the above choice is made, one can start the scan using the existing parameters, by clicking on "Continue with the Scan" or returning to the main menu for parameter or mode selection.

A flow chart that illustrates the scan process and data acquisition and storage is given in the Appendix.

4. Display

This command displays an image file acquired in a previous scan. The display of already acquired data/files uses the color vector saved along with the file or one currently in the system. The signals displayed on the monitor are in arbitrary units. The signals are converted into absolute units only at the time of final display by using normalizing parameters. {Saving the files: Each acquired image is saved automatically as the original data file by indexing the file number. The file number is displayed as follows. During the scan, the file name appears in a box directly under the box that describes the mode of operation (also see section on "Making measurements")}.

Dislocation density/GB mapping

The DD/GB mapping is currently done using Laser1 only. Later, we may incorporate a technique that will use both lasers to independently control the spatial resolution in DD mapping and optimize the GB definition. However, use of two lasers is required to make etch pit size corrections. This correction is needed only if problems with the etching process are suspected or identified. The standard dislocation samples will be provided to verify that the system is in calibration. If the calibration is required, go to the section on calibration.

FIG. 25 highlights the components of the SDMCS that participate in DD and GB mapping. It also shows how different signals are derived and connected to various channels during DD/GB mapping mode. This mode of operation requires measurement of signals from DD1, LPD1, and the GBD. To produce dislocation density and/or GB maps, use the following procedure.

Swing the IS into the optical path; make sure that the IS assembly is locked in the correct position.

Make sure the AA and the $T\lambda_1$ filter are in the optical path.

Turn Laser1 on (Laser2 off).

Place the test sample under the IS. Click on DD/GB mode to start the measurement procedure.

Place the attenuator in the optical path, swing the IS assembly out of the optical path; this will allow observation of the location of the optical beam on the sample.

Use Scan Area Definition to describe the scan dimensions.

Return to the main menu. Click on the Parameter Selection and choose parameter values.

Execute Scan Procedure. The screen will offer you options to select Laser1, Laser2, both lasers, or etch pit correction. Choose Laser1.

Swing IS assembly into position for measurement, and click on Continue with the Scan.

The etch pit size correction mode allows determination of the size of the etch pit if different from the standard size used in the calibration procedure. The size of the etch pits is used as a constant to correct for the dislocation density. The system will perform line scans across a selected cross section of the sample with Laser1 excitation. Next the system will ask the operator to turn off Laser1, and turn on Laser2. A line scan will be completed with Laser2 on. The computer will perform calculations on these data and determine a multiplication constant that will be used to correct the image data.

The system will go to the reference position and execute scan. The data will be acquired and displayed real-time as two images after each line scan is completed. The system will utilize the color vector defined in the previous display.

Notice that when displaying both GBs and DD, only one color sequence is being used. However, the operator can select color threshold for each map. This mode does not include a legend along with the images.

The system automatically assigns a file name in a sequential manner. These appear on the screen in the following format t7[3 character for the mode][3 digit number of scan].dat When the scan is complete, this condition appears on the screen.

Other information that appears during the scan, as shown in FIGS. 26–29:

Number of x-steps (samples)
Number of Y-steps( rows)
Step size
Area of the sample scanned
Type of scan mode (e.g. defect)
Laser1 or Laser2
Number of sample points per x-scan completed At the end of the scan, the operator may save the display file(s) or change the color vector to achieve a better contrast and/or range of the displayed parameter. One can go in the Display Mode to display individual image, readjust colors, and the color thresholds for optimum image contrast.

When the file is recalled under Display Mode, one can either recall both images or just one. If both images are recalled, the display does not include the color vector.

External LBIC-MODE

External LBIC can be operated with Laser1 or Laser2 or sequentially to determine either the near-surface recombination or the bulk recombination by using $\lambda=0.6328$ µm or $\lambda=0.905$ µm, respectively (FIG. 31). When operating LBIC at $\lambda=0.905$ µm, the system display the maps of the bulk recombination. However, this effect can be modulated by the reflectance effect. This analysis can still be useful in cases where reflectivity of the device is uniform, and in cases where the effect of reflectivity can be small compared to the changes in the surface and bulk properties.

Place the attenuator in the optical path

Swing the integrating sphere out of the optical path

Click on the External LBIC-mode to operate the system—the menu will guide you through the following operations Near-surface characteristics Turn Laser1 on (Laser2 off)

Set the gain constant for LPD1-channel to read LP1

Place the photovoltaic device on the X-Y scanning table, and use the Define Scan Area command to adjust the scan area. Select the scan area.

Check the gain constant setting on LBIC- channel displayed on the screen

Perform test scans (in standard Z- or Y-modulation) to determine the maximum signal (the LBIC amplifier gain is pre-set to ensure that the amplifier is not saturated due to the photo-current of the device)

Select the color vector for display

Scan

When the scan is completed the acquired LBIC image of the device can be adjusted to reset the offset and the range of the response variation. Select these parameters. The color vector will display the range of the response and the image corresponding to these parameters, as shown in FIG. 30.

The color scheme of the image can be readjusted by selecting the "image enhancement" subroutine, a simplified version of DCS.

The new image can be stored on the disk along with the corresponding color vector The color LBIC image can be printed as a hard copy using the color printer Reflectance measurement SDMCS can make both the specular and the diffuse reflectance maps simultaneously (schematic shown in FIG. 32 and maps shown in FIGS. 33 and 34). Specular reflectance is determined from the light component reflected within a 5° cone of the specularly reflected beam (later a provision will be made to adjust this angle to lower values). The specular reflectance is measured by the GBD. To measure the specular reflectance it is necessary to remove the AA to allow the entire reflected beam to be focused on the GBD. In the specular reflectance mode, the GBD is calibrated to read reflectance corresponding to excitation by each laser. This operation requires insertion of the appropriate filter $T\lambda_1$ or $T\lambda_2$ in the GBD path Specular reflectance at $\lambda_1$ Insert $T\lambda_1$ filter in the GBD path
Remove the AA from the GBD path
Place the test sample under the IS
Turn on Laser1
Click on the Reflectance mode box
Select use of Laser1 (this selects the correct detectors and channels for reading the signals).

For example, selecting reflectance measurements at $\lambda_1$ connects CH1 for LPD1, Ch5 for GBD, and incorporates appropriate gain values determined by the previous calibration.

Use Scan Area Definition command to define the scan area

Check the color vector for suitable color sequence, and color threshold

Follow the menu directions in the Specular Reflectance mode.

Diffuse reflectance

The diffuse reflectance is measured as the reflected, scattered light collected by the IS. DD1 and DD2 measure the diffused light corresponding to the incidence of Laser1 and Laser2, respectively.

To measure the diffuse reflectance at wavelength $\lambda_1$,

Place the test sample under the IS
Turn on Laser1
Click on the Reflectance mode box
Select use of Laser1—Use Scan Area Definition command to define the scan area Check the color vector for suitable color sequence, and color threshold follow the menu directions in the Diffuse Reflectance mode.

MINORITY CARRIER DIFFUSION LENGTH MAPPING

Requires two measurements—one consisting of the LBIC with Laser2 on, and the other of Reflectance with Laser2 on (schematic shown in FIG. 35). The system is pre-calibrated to read mA/mW. To convert LBIC signal into the minority carrier diffusion length the response of a cell, fabricated by the same process as used in the test cell fabrication, is pre-stored in the computer as the calibration constant. Select the suitable calibration constant.

Swing the integrating sphere out of the optical path

Click on the MCDL-mode to operate the system—the menu will guide you through the following operations MCDL mapping—Turn Laser2 on (Laser1 off)

Set the gain constant for LPD2-channel to read LP2

Place the photovoltaic device on the X-Y scanning table, and use the computer to adjust the scan area. Select the scan area.

Check the gain constant setting on MCDL- channel displayed on the screen for the type of the device (determined by the device processing conditions)

Perform test scans (in standard Z- or Y-modulation) to determine the maximum signal (the MCDL- amplifier gain is pre-set to ensure that the amplifier is not saturated due to the photo-current of the device)

Select the color vector for display
Scan

When the scan is completed the acquired MCDL image of the device can be adjusted to reset the off-set and the range of the response variation. Select these parameters. The color vector will display the range of the response and the image corresponding to these parameters.

The original MCDL image may be saved on the disk

The color scheme of the image can be readjusted by selecting the "image enhancement" subroutine.

The new image can be stored on the disk along with the corresponding color vector The color MCDL- image can be printed as a hard copy using the color printer The MCDL-imaging for a device with varying (or unknown) reflectance characteristics requires measurement of reflectance to determine internal photoresponse map (at $\lambda=0.905$ mm). This is particularly necessary for polycrystalline cells that have textured or rough surfaces.

The standard cell is also calibrated in terms of the minority carrier diffusion length. The system is pre-calibrated to display mA/mW in the LBIC mode. This is directly related to the minority carrier diffusion length. Unfortunately, one cannot use this current to relate to the minority carrier diffusion length in all cases because the collection efficiency of different cells can vary. However, for a given cell process one may be able to use the ratio of currents at two different wavelengths to overcome this problem.

CALIBRATING THE SYSTEM

SDMCS requires calibration of various detectors in order to easily measure reflectance values, convert reflectance measurements made on the defect etched samples in terms of the dislocation density, and measure photo-induced current by the incident light power. To accomplish this, the laser power detectors are calibrated directly to read the power incident on the sample—the GBD, DD1, and DD2 are calibrated to read power reflected by the test wafers. The calibration constants are stored in the computer for each wavelength of operation LBIC amplifier is a low input impedance system and is calibrated to directly read mA. Since the LBIC measurement is done in a short circuit configuration, the device size, and the beam size are relatively unimportant.

the minority carrier diffusion length is determined directly from the magnitude of current induced by the long wavelength excitation. This measurement is influenced by the collection efficiency of the device. However, by using reference cells fabricated by a process the same as or similar to the test cell, this error is minimized.

All the calibration procedures are based on the following assumptions:

The response of all detectors is linear in the range of operation.

All detectors have a preset preamplifier gain. This gain is adjusted to ensure low-noise operation in the measurement range for which it is used.

The output of each detector-preamplifier is hard-wired to fixed channels on the computer board. The channel gain of the board is changed automatically to appropriate values as determined by calibration (if the same channel is active in more than one mode of system operation). For example, GBD is used for GB measurement and specular reflectance measurement at both $\lambda_1$ and $\lambda_2$. In each of the measurements the filters are changed accordingly. The loss due to filter transmittance is compensated by the channel gain (and not in the preamplifier gain).

The following channels are assigned to various detectors

DD1 — CH 0    GBD — CH 1    LBIC — CH 2
DD2 — CH 3    LPD1 — CH 4   LPD2 — CH 5

The preamplifier gain is large enough to provide suitable input to the computer board even for the lowest value of the signal The calibration procedures ensure that the normalized signals after the computer board measure the corresponding parameter The signal in a channel=Detector signal×Preamplifier gain×channel gain The detector-preamplifier gains are preset; the channel gain is the gain in the computer board and can be adjusted in the computer software. In addition, the computer may multiply a file or files by appropriate constants to ensure correct normalization.

All calibration procedures should be done after the optical alignment of the system is made. A recalibration may be necessary if alignment is disturbed.

CALIBRATION OF THE LASER-POWER DETECTORS
Configuration 1.

Turn Laser1 on and measure LPD1, (Laser2 off)
Relationship between LPD1 signal and laser power $$SLPD1 = R1 * P1$$

$$PS1 = P1 * T1 * T2$$
$$\text{Power delivered to the sample,} = P1 * (1 - R1) * T2$$
$$= \text{constant} * P1$$

where R1 and T1 are the reflectance and the transmittance, respectively, of the beam splitter BS1, and T2 is the transmittance of the beam splitter BS2.

Turn Laser1 off, turn Laser2 on, and measure LPD2

$$SLPD2 = T2 * P2$$

Power delivered to the sample,
PS2 = P2 * R2
= constant * P2

Constants for P1 and P2 are pre-calibrated. To perform this calibration, a standard detector is placed in the test plane and the absolute power from the Laser1 and Laser2 are measured. This is the power that is incident on the sample during measurement. Next, the standard power meter is placed in the place of LPD1 and LPD2, sequentially, and the powers in the laser beams are read. These measurements are used to determine the constants that relate PS1 and P1, and PS2 and P2.

Configuration 2.

Configuration 2 measures the laser power directly at the sample plane by means of a calibrated detector (a solar cell). This solar cell is provided with the calibrated spectral response in terms of mA/mW (particularly at the wavelengths of the lasers). Thus, this detector can directly measure the light incident on the test samples and can read the laser power at the sample as well.

To measure the laser power at the sample:

Place the reference detector under the integrating sphere.
Turn Laser1 on and read the incident power. Enter this power in the calibration program as the value of PS1.
Turn Laser1 off, and turn Laser2 on, and read the power. Enter this power in the calibration program as the value of PS2.

Note: All calculations use laser power incident on the sample to determine parameters such as reflectance, LBIC signal, and dislocation density. These quantities are calculated in configuration 1, and directly measured in configuration 2. As will be apparent, configuration 1 is easier to the user who is primarily interested in applications of the system because the calibration processes are needed very infrequently. Configuration 2 involves more frequent use of calibrated detectors, but the system and the calibration process are simpler.

REFLECTANCE CALIBRATION

SDMCS will measure both the specular and the diffuse reflectance of samples and produce spatial maps of these parameters. Each of these parameters can be measured at the light wavelengths available for the system.

Reflectance measurements use LPD1 and LPD2 to directly read the power incident on the sample (see calibration of LPD1 and LPD2). The relation between P1 and the signal from LPD1, is $$S_{LPD1} \times G_{LPD1-PA1} \times G_{CH1} = P1$$

Likewise, $$S_{LPD2} \times G_{LPD2-PA2} \times G_{CH2} = P2$$

$G_{LPD1-PA1}$ is the gain in the preamplifier 1, and $G_{CH1}$ is the gain in the computer board.

The GBD is set with a constant preamplifier gain; the channel gains are adjusted for operation at each wavelength $\lambda_1$ and $\lambda_2$. The channel gain is set for each wavelength operation such that, when the corresponding filter is in place, the GBD reads the reflected power from the sample.

$$S_{GBD}(\lambda_1) \times G_{GBD-PA5} \times G_{CH5}(\lambda_1) = \text{Reflectance}(\lambda_1)$$

$$S_{GBD}(\lambda_2) \times G_{GBD-PA5} \times G_{CH5}(\lambda_2) = \text{Reflectance}(\lambda_2)$$

DD1 and DD2 are set up such that with the corresponding filter in front of the detector, the detector signal×amplifier gain×channel gain=the absolute power.

$$S_{DD1}(\lambda_1) \times G_{GBD-PA3} \times G_{CH3}(\lambda_1) = \text{Reflectance}(\lambda_1)$$

$$S_{DD2}(\lambda_2) \times G_{GBD-PA4} \times G_{CH4}(\lambda_2) = \text{Reflectance}(\lambda_2)$$

To calibrate the specular reflectance, $\{Rs(\lambda_1)\}$, at the wavelength $\lambda_1$, place the standard reflectance sample consisting of a polished silicon wafer, in the sample position. Remove the stop in front of the lens in the GB path to allow the entire specular component of the light to reach the GBD, and turn on the laser of wavelength $\lambda_1$. Measure the current in the GB detector, (GBD), and the current in the reference detector (that measures the laser power incident on the standard sample). Determine the ratio R1(SGBD/SLPD1).

The reflectance of the sample at $\lambda_1$ is A. This determines the calibration constant as A/R1.

Calibrating the specular reflectance channel

1. Select the appropriate calibration mode depending on the laser to be used. For example, Laser1 calibration functions.
2. Insert specular reflectance standard sample (SRSS) under the integrating sphere.
3. Remove the annular aperture (AA) from the path of GBD, make sure filter $T\lambda_1$ is in the optical path
4. Turn on Laser1
5. The computer will display the GBD signal ($S_{GBD}$), and the LPD1 signal, $S_{LPD1}$ SGBD/($S_{LPD1} \times G_{CH1}$) should be equal to the reflectance of Si (equal to 0.4). Select the channel gain accordingly.
6. Adjust the channel gain=$S_{GBD}$/0.4 * $S_{LPD1}$ The above procedure should be performed for both lasers with the appropriate values of reflectance.

To measure the calibration constant for the diffuse reflectance

Place the standard diffuse reflectance sample under the integrating sphere. Turn on Laser1, and measure the signal in the dislocation detector DD1. The calibration constant for the diffuse reflectance=DD1/LP1.

NOTE: In the diffuse reflectance measurement a part of the scattered light is lost through various apertures. Although, the reflectance of solar cells is not truly Lambertian which can cause a certain error in the diffuse component. However, this error is very small in the measurement of the total reflectance.

Total reflectance=specular reflectance+diffuse reflectance

{Here, we define specular reflectance as the reflectance within a solid angle which is determined by the input aperture of the integrating sphere.}

The above procedure should be performed for both lasers.

To determine cross talk between the specular reflectance (SR) channel and the diffuse reflectance (DR) channel, read DD1 and DD2 signals.

The system is ready for SR measurement. Place the test sample under the integrating sphere. Align the sample for scanning and scan. Replace the AA in the GBD path.

DISLOCATION DENSITY CALIBRATION

In this mode the computer will measure light intensity illuminating the sample, and the signal from DD1. Standard dislocation density sample is provided with its DD identified or with a calibrated dislocation density map. Place the SDDS under the IS and make the measurement.

LBIC CALIBRATION

The LBIC signal is measured in terms of mA/mW. The external LBIC simply measures the current due to the incident laser power. The current amplifier of the SDMCS is calibrated to produce known gains (controllable by the circuit configuration as well as by the computer). The output of the amplifier is calibrated to directly read this signal. This signal is displayed on the computer as:

(photo-current in mA)×(amplifier gain)×(gain due to the computer board). In the LBIC mode, the amplifier is adjusted to read mA/mW This is accomplished by means of a reference cell, of known mA/mW at each of the wavelengths.

Reflectance mode

All detectors are pre-calibrated to read power, hence each laser power detector directly measures the fraction of the laser output reaching the detector. The corresponding constant (Ci) is predetermined and needs to be rarely checked.

Dislocation detectors, DD1 and DD2 are pre-calibrated to read diffuse reflectance; however, this calibration is checked routinely by means of a standard diffuse reflectance sample.

The diffuse reflectance (1) = Power measured by (DD1)/laser power(1)
= Signal at DD1 * D1/Signal at LPD1 * C1

The diffuse reflectance (2) = Power measured by (DD1)/laser power(1)
= Signal at DD2 * D2/Signal at LPD2 * C2

An alternate approach for calibration, that does not require detectors DD1 and DD2, consists of using a calibrated solar cell to directly measure light power incident on the test samples. The short circuit current output of the calibrated cell is monitored through the same channel as that used for LBIC measurements.

Dislocation density detector is calibrated by using two standard samples to measure their diffuse reflectance.

Measure the incident light power

Place the standard sample under the integrating sphere and measure the DD1 signal.

Adjust the gain of the detector to read the diffuse reflectance

When the detector is adjusted to read the diffuse reflectance, the standard dislocation sample can then be used to adjust the gain of the channel such that the signal is 1 for a dislocation density of $10^6$/cm$^2$.

Note that the DD detectors are adjusted to read reflectance. Then the gain of each dislocation channel is adjusted to read dislocation density. This gain must be set by the software while in the dislocation mode.

As can be appreciated, the present invention allows for calibrated, compensated, absolute (as opposed to relative) values to be obtained for the characteristics of the semiconductor material, such as dislocation defect density, grain boundaries, reflectance, external LBIC, internal LBIC, and minority carrier diffusion length.

The foregoing description is considered as illustrative only of the principles of the invention. Furthermore, since numerous modifications and changes will readily occur to those skilled in the art, it is not desired to limit the invention to the exact construction and process shown as described above. For example, and without limitation, the present invention would be applicable to scanning electron microscopes. Further, the analog display controller and associated recorder and scope may not be necessary since sufficient resolution is now available with the digital computer, monitor, and printer combination. Further still, with increased resolution by the detectors, the sophistication of the beam splitters is of lesser importance and quartz plates without anti-reflective coatings can be used. Accordingly, all suitable modifications and equivalents may be resorted to falling within the scope of the invention as defined by the claims which follow.

The embodiments of the invention in which an exclusive property or privilege is claimed are defined as follows:

1. A method of measuring characteristics of a piece of material, wherein the piece of material includes a photovoltaic device, comprising the steps of:

exposing the piece of material to incoming light of a known level of power;

determining the power level of the light reflected from the piece of material;

calculating the amount of light absorbed by the piece of material based upon the power level of the light exposed and the power level of the light reflected;

measuring an electrical current induced through the photovoltaic device by the incoming light;

calculating the conversion efficiency of the photovoltaic device based upon the calculation of the amount of light absorbed by the device and the electrical current induced therethrough; and compensating for inaccuracies in the known level of power, in the determination of the power level of the reflected light, and in the measurement of induced electrical current to achieve a compensated calculation of the conversion efficiency.

2. A method as defined in claim 1, wherein the compensating step includes:

substituting a standard sample device for the photovoltaic device, the sample device having a known conversion efficiency;

performing the exposing, determining, calculating the amount of light, measuring, and calculating the conversion efficiency steps; and using the ratio of the known conversion efficiency of the standard sample device to the calculated conversion efficiency of the standard sample device as a compensation factor.

3. A method of measuring defects in a piece of semiconductor material, comprising the steps of:

exposing the piece of semiconductor material to incoming light;

detecting light specularly reflected by the piece of semiconductor material as an indication of the magnitude of a first type of defect in the material; and detecting light diffusely reflected by the piece of semiconductor material as an indication of the magnitude of a second type of defect in the material; and compensating for inaccuracies in the detection of the light specularly and diffusely reflected to achieve a compensated calculation of the magnitude of the first and second type of defects.

4. A method as defined in claim 3, wherein the compensating step includes:

substituting a first and a second standard sample for the piece of material, the first standard sample having a known magnitude of the first type of defect and the second standard sample having a known magnitude of the second type of defect;

performing the exposing and each of the detecting steps; and using the ratio of the known magnitude of the first type of defect to the indicated magnitude from the detected specularly-reflected light and the ratio of the second type of defect to the indicated magnitude from the detected diffusely-reflected light as compensation factors.

5. A system for measuring characteristics of a piece of material, wherein the piece of material includes a photovoltaic device, comprising:

means for exposing the piece of material to incoming light of a known level of power;

means for determining the power level of the light reflected from the piece of material;

means for calculating the amount of light absorbed by the piece of material based upon the power level of the light exposed and the power level of the light reflected;

means for measuring an electrical current induced through the photovoltaic device by the incoming light;

means for calculating the conversion efficiency of the photovoltaic device based upon the calculation of the amount of light absorbed by the device and the electrical current induced therethrough; and means for compensating for inaccuracies in the known level of power, in the determination of the power level of the reflected light, and in the measurement of induced electrical current to achieve a compensated calculation of the conversion efficiency.

6. A system as defined in claim 5, wherein the means for compensating includes:

means for substituting a standard sample device for the photovoltaic device, the sample device having a known conversion efficiency; and wherein the ratio of the known conversion efficiency of the standard sample device to the conversion efficiency of the standard sample device calculated by the calculating means is used as a compensation factor.

7. A system for measuring defects in a piece of semiconductor material, comprising:

means for exposing the piece of semiconductor material to incoming light;

means for detecting light specularly reflected by the piece of semiconductor material as an indication of the magnitude of a first type of defect in the material; and means for detecting light diffusely reflected by the piece of semiconductor material as an indication of the magnitude of a second type of defect in the material; and means for compensating for inaccuracies in the detection of the light specularly and diffusely reflected to achieve a compensated calculation of the magnitude of the first and second type of defects.

8. A system as defined in claim 7, wherein the means for compensating includes:

means for substituting a first and a second standard sample for the piece of material, the first standard sample having a known magnitude of the first type of defect and the second standard sample having a known magnitude of the second type of defect; and wherein the ratio of the known magnitude of the first type of defect to the indicated magnitude from the detected specularly-reflected light and the ratio of the second type of defect to the indicated magnitude from the detected diffusely-reflected light are used as compensation factors.

9. A method for detecting and distinguishing between a first type of defect and a second type of defect in the surface of a crystalline material, comprising the steps of:

preparing said surface in such a manner that said first type of defect scatters incident light in a first pattern and said second type of defect scatters incident light in a second pattern;

illuminating said surface with incident light and scattering said incident light from said surface to create said first pattern and said second pattern;

separating at least some of the scattered light in said first pattern from at least some of the scattered light in the second pattern;

detecting the scattered light of said first pattern as an indication of the magnitude of said first type of defect in the surface of the crystalline material;

detecting the scattered light of said second pattern as an indication of the magnitude of said second type of defect in the surface of the crystalline material; and compensating for inaccuracies in the detection of the light reflected of said first pattern and of said second pattern to achieve a compensated calculation of the magnitude of each of the first and second types of defects by substituting a standard sample for the crystalline material, the sample having a known magnitude of each of the first and second types of defects, and after separately performing the illuminating, separating, and each of the detecting steps on the standard sample, using the ratio of the known magnitude of each defect in the standard sample to the indicated magnitude from each of the patterns of detected light for the standard sample as compensation factors for the calculation of each of the first and second types of defect.

10. A method of measuring characteristics of a piece of material, wherein the piece of material includes a photovoltaic device, comprising the steps of:

exposing the piece of material to incoming light of a known level of power;

measuring an electrical current induced through the photovoltaic device by the incoming light;

calculating the conversion efficiency of the photovoltaic device based upon the known power level of the light to which the device was exposed and the electrical current induced therethrough; and compensating for inaccuracies in the known level of power and in the measurement of induced electrical current to achieve a compensated calculation of the conversion efficiency.

11. A system for measuring characteristics of a piece of material, wherein the piece of material includes a photovoltaic device, comprising:

means for exposing the piece of material to incoming light of a known level of power;

means for measuring an electrical current induced through the photovoltaic device by the incoming light; and means for calculating the conversion efficiency of the photovoltaic device based upon the known power level of the light to which the device was exposed and the electrical current induced therethrough; and means for compensating for inaccuracies in the known level of power and in the measurement of induced electrical current to achieve a compensated calculation of the conversion efficiency.

12. An apparatus for detecting and distinguishing between a first type of defect and a second type of defect in the surface of a crystalline material, after the surface has been prepared in such a manner that said first type of defect scatters incident light in a first pattern and said second type of defect scatters incident light in a second pattern, the apparatus comprising:

means for illuminating said surface with incident light and scattering said incident light from said surface to create said first pattern and said second pattern;

means for separating at least some of the scattered light in said first pattern from at least some of the scattered light in the second pattern;

means for detecting the scattered light of said first pattern as an indication of the magnitude of said first type of defect in the surface of the crystalline material;

means for detecting the scattered light of said second pattern as an indication of the magnitude of said second type of defect in the surface of the crystalline material; and means for compensating for inaccuracies in the detection of the light reflected of said first pattern and of said second pattern to achieve a compensated calculation of the magnitude of each of the first and second types of defects by substituting a standard sample for the crystalline material, the sample having a known magnitude of each of the first and second types of defects, then utilizing the illuminating, separating, and each of the detecting means to determine the indicated magnitude of each of the defects in the standard sample, and using the ratio of the known magnitude of each defect in the standard sample to the indicated magnitude from each of the patterns of detected light from the standard sample as compensation factors for the calculation of each of the first and second types of defect in the crystalline material.

* * * * *